US011525773B2

(12) United States Patent
Fang et al.

(10) Patent No.: US 11,525,773 B2
(45) Date of Patent: Dec. 13, 2022

(54) READING APPARATUS

(71) Applicants: Zhejiang Orient Gene Biotech Co., Ltd, Huzhou (CN); Healgen Scientific Limited, Houston, TX (US)

(72) Inventors: Jianqiu Fang, Huzhou (CN); Fangzhou Xu, Huzhou (CN); Xiulong Ge, Huzhou (CN)

(73) Assignees: ZHEJIANG ORIENT GENE BIOTECH CO., LTD., Huzhou (CN); HEALGEN SCIENTIFIC LIMITED

( * ) Notice: Subject to any disclaimer, the term of this patent is extended or adjusted under 35 U.S.C. 154(b) by 731 days.

(21) Appl. No.: 16/517,027

(22) Filed: Jul. 19, 2019

(65) Prior Publication Data
US 2020/0225147 A1 Jul. 16, 2020

(30) Foreign Application Priority Data

Jan. 10, 2019 (CN) .......................... 201910023743.3
Apr. 4, 2019 (CN) .......................... 201910269927.8

(51) Int. Cl.
*G01N 21/27* (2006.01)
*G01N 21/55* (2014.01)
(Continued)

(52) U.S. Cl.
CPC ............. *G01N 21/27* (2013.01); *G01N 21/55* (2013.01); *G01N 33/54386* (2013.01);
(Continued)

(58) Field of Classification Search
CPC ............. G01N 21/8483; G01N 33/558; G01N 2201/062; G01N 2021/8488;
(Continued)

(56) References Cited

U.S. PATENT DOCUMENTS

| 2005/0037511 A1* | 2/2005 | Sharrock | G01N 21/251 436/164 |
| 2011/0184651 A1* | 7/2011 | Weng | G01N 33/558 702/22 |
| 2016/0187333 A1* | 6/2016 | Moll | B01L 3/502715 506/18 |

FOREIGN PATENT DOCUMENTS

| CA | 2638861 A1 * | 3/2009 | ......... G01N 21/6428 |
| CN | 101545864 A * | 9/2009 | |

(Continued)

*Primary Examiner* — Michael P Stafira
(74) *Attorney, Agent, or Firm* — NZ Carr Law Office

(57) ABSTRACT

The present invention relates to the field of biochemical detection, and in particular to a reading apparatus for reading an assay result on a testing element. The reading apparatus comprises a first light-emitting element, a first photodetector and a light blocking element, wherein the first light-emitting element emits light and illuminates one or more corresponding areas of the testing element, the first photodetector receives light from one or more corresponding areas of the testing element, and the light blocking element guides a path of light emitted from a light emitting element and/or from a testing element. The light blocking element separates photodetectors in separate spaces, including a first light blocking element and a second light blocking element, wherein the first light blocking element is located between the first light-emitting element and the first photodetector, to guide the light emitted from the light emitting element to illuminate the testing element. The reading apparatus of the present invention allows light from a specific area of the testing element to be received by the photodetector and blocks invalid light from unrelated areas from entering the photodetector, thereby enhancing the accuracy and sensitivity of detection.

15 Claims, 6 Drawing Sheets

(51) Int. Cl.
*G01N 33/543* (2006.01)
*G01N 21/17* (2006.01)
*G01N 21/59* (2006.01)

(52) U.S. Cl.
CPC ........... *G01N 2021/1761* (2013.01); *G01N 2021/5969* (2013.01); *G01N 2201/062* (2013.01)

(58) Field of Classification Search
CPC ......... G01N 21/274; G01N 2021/8494; G01N 21/78; G01N 21/76; G01N 2201/06106; G01N 33/54366; G01N 33/582; G01N 21/6452; G01N 21/6428; G01N 35/04; G01N 35/00732; G01N 2021/6439; G01N 15/1459; G01N 2333/59; G01N 33/76; G01N 2035/0425; G01N 21/645; G01N 33/54313; G01N 33/689; G01N 21/4738; G01N 21/66; G01N 33/585; G01N 35/1002; G01N 15/14; G01N 2035/00752; G01N 33/54386; G01N 35/0099; G01N 2015/0038; G01N 2015/1493; G01N 2800/52; G01N 35/0098; G01N 35/028; G01N 35/1079; G01N 21/253; G01N 33/58; G01N 33/6863; G01N 15/1425; G01N 2035/0415; G01N 2035/0465; G01N 2035/0475; G01N 21/05; G01N 33/543; G01N 35/1081; G01N 2035/1025; G01N 33/54373; G01N 35/1011; G01N 31/22; G01N 33/5302; G01N 35/0092; G01N 21/648; G01N 2333/7158; G01N 33/533; G01N 2035/1076; G01N 2201/0221; G01N 2201/12; G01N 2458/00; G01N 33/50; G01N 33/545; G01N 2021/6441; G01N 2035/1051; G01N 21/55; G01N 21/77; G01N 33/53; G01N 33/57407; G01N 33/6893; G01N 33/74; G01N 1/31; G01N 1/38; G01N 2015/1006; G01N 2035/00435; G01N 2035/00851; G01N 2035/0405; G01N 2035/0413; G01N 2035/0436; G01N 2035/1013; G01N 2035/1048; G01N 21/00; G01N 21/6486; G01N 2333/5752; G01N 35/00; G01N 35/1016; G01N 2035/00881; G01N 21/27; G01N 21/31; G01N 21/6408; G01N 21/7703; G01N 33/54326; G01N 2021/7759; G01N 2021/7773; G01N 21/6456; G01N 21/6458; G01N 21/69; G01N 2333/54; G01N 27/3273; G01N 33/523; G01N 33/526; G01N 33/536; G01N 33/54346; G01N 33/574; G01N 33/57426; G01N 33/57484; G01N 33/6869; G01N 35/00722; G01N 1/00; G01N 15/1436; G01N 15/1468; G01N 15/147; G01N 15/1484; G01N 2015/144; G01N 2035/0453; G01N 2035/0467; G01N 2035/0498; G01N 2035/1032; G01N 21/47; G01N 21/553; G01N 2333/521; G01N 2333/522; G01N 33/54393; G01N 33/5743; G01N 33/57488; G01N 33/57492; G01N 33/57496; G01N 33/66; G01N 33/94; G01N 35/00871; G01N 35/025; G01N 35/026; G01N 15/1463; G01N 15/1475; G01N 2015/1452; G01N 2021/0325; G01N 2035/00495; G01N 2035/0406; G01N 21/25; G01N 21/64; G01N 2201/0648; G01N 2201/068; G01N 2800/60; G01N 33/491; G01N 35/00584; G01N 35/00603; G01N 35/109; G01N 2021/0346; G01N 2035/00356; G01N 2035/042; G01N 2035/0494; G01N 21/86; G01N 33/5091; G01N 33/535; G01N 33/56972; G01N 33/56983; G01N 33/588; G01N 33/68; G01N 35/02; G01N 15/1429; G01N 2015/1486; G01N 2021/635; G01N 2201/0642; G01N 2201/0833; G01N 2800/24; G01N 33/5047; G01N 33/505; G01N 33/5304; G01N 33/54306; G01N 33/57434; G01N 33/6854; G01N 2021/1761; G01N 2021/4707; G01N 2021/5969; G01N 2021/6463; G01N 2021/6465; G01N 2021/6471; G01N 2035/00108; G01N 2035/00326; G01N 2035/00346; G01N 21/01; G01N 21/03; G01N 21/0303; G01N 21/13; G01N 21/251; G01N 21/763; G01N 21/82; G01N 21/9036; G01N 21/909; G01N 2201/0612; G01N 2201/0621; G01N 2201/064; G01N 2201/08; G01N 2201/084; G01N 2333/005; G01N 2333/195; G01N 2333/70596; G01N 2458/30; G01N 2800/2871; G01N 2800/56; G01N 33/48; G01N 33/5306; G01N 33/581; G01N 35/00029; G01N 35/10; G01N 35/1065; G01N 1/28; G01N 15/06; G01N 15/0612; G01N 15/1404; G01N 2015/0065; G01N 2021/0389; G01N 2021/174; G01N 2021/1765; G01N 2035/00772; G01N 2035/00891; G01N 2035/0091; G01N 2035/0486; G01N 2223/40; G01N 2223/401; G01N 2223/413; G01N 2223/421; G01N 2333/161; G01N 2333/525; G01N 2333/70578; G01N 2570/00; G01N 27/3271; G01N 2800/26; G01N 2800/7095; G01N 33/48707; G01N 33/4875; G01N 33/5002; G01N 33/5094; G01N 33/5308; G01N 33/552; G01N 33/564; G01N 33/56966; G01N 33/57449; G01N 33/587; G01N 33/6809; G01N 33/78; G01N 33/80; G01N 1/30; G01N 2021/478; G01N 2021/5957; G01N 2021/6419; G01N 2021/6421; G01N 2021/7786; G01N 21/07; G01N 21/4788; G01N 21/532; G01N 21/6402; G01N 21/6445; G01N 21/658; G01N 2201/0231; G01N 2333/485; G01N 2333/705; G01N 2333/71; G01N 2500/00; G01N 2500/04; G01N 2500/10; G01N 2800/50; G01N 33/02; G01N 33/493; G01N 33/52; G01N 33/5438; G01N 33/54388; G01N 33/566; G01N 33/57419; G01N 33/583; G01N 33/6842;

G01N 33/6848; G01N 33/6872; G01N 33/82; G01N 35/00069
See application file for complete search history.

(56) References Cited

FOREIGN PATENT DOCUMENTS

CN 202486051 U * 10/2012
DE 202010005871 U1 * 9/2010 ......... G01N 21/8483

* cited by examiner

READING APPARATUS

CROSS REFERENCE TO RELATED APPLICATION

The present application claims the benefit of Chinese Patent Application No. 201910023743.3, filed on Jan. 10, 2019, and Chinese Patent Application No. 201910269927.8, filed on Apr. 4, 2019. The content of these applications including all tables, diagrams and claims is incorporated hereby as reference it its entirety.

FIELD OF THE INVENTION

The present invention relates to the field of biochemical detection, and in particular to a reading apparatus for reading an assay result in conjunction with a testing element using a biological immunoassay method.

BACKGROUND OF THE INVENTION

At present, the detection apparatus for detecting the presence or absence of analyte in sample is widely used in hospitals or homes, and such apparatus for rapid diagnosis comprises one or more test strips, such as early pregnancy detection, drug abuse detection, etc. The apparatus is very convenient, and the detection result can be obtained within one minute or at most ten minutes. An electronic reader is used together with a test carrier such as a test strip to detect the concentration and/or amount of analyte in a fluid sample, to visually read the detection results.

U.S. Pat. No. 5,580,794 discloses a disposable integrated analytical reader and lateral flow test strip. Detection results are obtained by measuring the reflected light using optical elements in the reader. However, this apparatus has some defects. When a plurality of light emitting elements irradiate corresponding areas in a narrow test strip, the light reflected or transmitted from the corresponding areas cannot be irradiated only to one or more photodetectors and light from the light source may go directly to the photodetectors, affecting the accuracy of detection results.

U.S. Pat. No. 7,315,378 provides a solution to this problem by providing a baffle between a light emitting element and a photodetector, to prevent direct light from the light emitting element from shining onto the photodetector. However, these apparatuses still need to be improved, in particular, when multiple different tests need to be performed simultaneously on a test strip, the photoelectric detector should be able to accurately reflect the signal changes in the specific testing area and avoid the interference of reflected light from other non-testing areas.

Chinese Patent Publication No. CN101650298 discloses an analytical reader used together with a test strip. The reader comprises one or more light sources, the light from light sources emit to at least two spatially separated areas on the test strip, and one or more photodetectors are used to detect lights emitted from each of the two areas of the test strip. In order to ensure that each light source can only illuminate the corresponding area of the test strip, each light source is optically separated by an opaque baffle, and a ramp-shaped component is disposed between the light source and the photodetector to prevent light from the light source from directly shining on the photodetector. The test strip is located above the light source of the reader without covering the photodetector, making the reader relatively large. In addition, the distance between the light source and the photodetector needs to be controlled precisely. If the distance is too far, the photodetector will not be able to receive the lights reflected by the test strip.

Chinese Patent Publication No. CN104730229 discloses an electronic detection apparatus for analyzing test strips used for assay and detection, which comprises an intersecting first separator and a second separator. The first separator includes a light source separator and an anti-scattering separator. The light source separator separates a plurality of light sources into two groups at the position of the light source, and separates the testing area of the test strip from the blank area. The anti-scattering separator separates the testing area of the test strip from the blank area, and the second separator separates the light source from the photodetector, to prevent mutual interference of lights between the blank area and the testing area, and between the light emitting area and the receiving area.

There are many limitations when it is necessary to read the final test results very sensitively with the signal changes on the testing area of the test strip. So, it requires further improvements to the traditional design, so as to improve the detection accuracy and sensitivity.

SUMMARY OF THE INVENTION

The present invention provides a reading apparatus for reading an assay result on a testing element. The apparatus allows more light from the testing element to emit to the photodetector, in particular, valid light from the testing element that can reflect the detection results are detected by the photodetector, avoiding the influence of other stray lights.

In a first aspect herein, the present invention provides a reading apparatus for reading an assay result, comprising: a first light-emitting element, emitting light and illuminating one or more corresponding areas of a testing element; and a first photodetector, receiving light from one or more corresponding areas of the testing element.

In some preferred embodiments, the apparatus further comprises a light blocking element for guiding a path of light from the light emitting element and/or the testing element. In some embodiments, the light blocking element blocks light from the light emitting element from directly illuminating the photodetector. In some embodiments, the light blocking element allows light from a specific area of the testing element to be received by the photodetector, while blocking the light from other area from being substantially received by the photodetector. In some embodiments, the specific area may be a testing area and/or a control area, the other area may be an area before the testing area or the control area, and/or an area between the testing area and the control area, for example, a reference area, a mark area, and a water absorption area, etc.

In some embodiments, when having a testing element, the light blocking element is located between the photodetector and the testing element, to block part of area of the testing element from receiving lights emitted by the light emitting element, or block the lights emitted from part of area of the testing element from illuminating the photodetector. In some embodiments, the light blocking element is longitudinally parallel to the testing element. In some embodiments, the light blocking element is in contact with some areas of the testing element.

In some embodiments, the light blocking element guides a path of light emitted from a light emitting element and/or from a testing element such that the light emitting element illuminates a specific area of the testing element or the light from the testing element (e.g. a specific area) is received by the photodetector as much as possible.

In some preferred embodiments, the light blocking element comprises a first light blocking element and a second light blocking element, the light blocking element separates photodetectors in separate spaces, wherein the first light blocking element is located between the first light-emitting element and the first photodetector, to guide the light emitted from the light emitting element to illuminate one or more areas of the testing element.

In some preferred embodiments, the second light blocking element allows light from a testing element or light from a specific area to be received by the photodetector.

Preferably, the second light blocking element is located above the first photodetector.

Preferably, the second light blocking element is disposed between the first photodetector and the testing element.

Preferably, the extension of the first light blocking element intersects the testing element, and the second light blocking element is longitudinally parallel to the testing element.

Preferably, the second light blocking element and the first light blocking element are disposed in a mutually perpendicular form.

Preferably, the first light blocking element cooperates with the second light blocking element to guide the light emitted by the light emitting element to illuminate one or more areas of the testing element, and allow the light from the testing element or the light from a specific area of the testing element to be received by the photodetector.

Preferably, the first light blocking element guides the light emitted by the light emitting element to illuminate the testing element, and the second light blocking element guides the light from the testing element to illuminate the first photodetector.

Preferably, the first light blocking element guides the light emitted by the light emitting element to illuminate the testing element, without illuminating the first photodetector.

Preferably, the apparatus further comprises a third light blocking element, wherein the first photodetector is located between the first light blocking element and the third light blocking element.

Preferably, the second light blocking element is located between the first light blocking element and the third light blocking element and covers the first photodetector.

Preferably, the second light blocking element is disposed in an area between the testing area and the control area of the testing element.

Preferably, the apparatus further comprises a second light-emitting element, wherein the second light-emitting element is disposed outside the third light blocking element.

Preferably, the first light-emitting element and the first photodetector are linearly arranged, or the first light-emitting element and/or the second light-emitting element are/is linearly arranged with the first photodetector.

Preferably, the light blocking element has a gap that transmits light from the testing element.

Preferably, the gap is disposed at a position corresponding to a testing area or a control area of the testing element.

Preferably, the gap is formed by providing a certain space between the first light blocking element and the second light blocking element.

Preferably, the gap is a slanted gap.

Preferably, the apparatus further comprises a lateral flow testing element, wherein the testing element comprises a testing area and a control area.

In one preferred embodiment, the present invention provides a reading apparatus for reading an assay result on a testing element, wherein the apparatus comprising:

a first light-emitting element and a second light-emitting element, emitting light and illuminating one or more corresponding areas of a testing element;

a first photodetector, receiving light from one or more corresponding areas of the testing element;

a light blocking element, for guiding a path of light emitted from a light emitting element and/or from a testing element, wherein the light blocking elements include a first light blocking element, a second light blocking element and a third light blocking element, wherein the first photodetector is located between the first light blocking element and the third light blocking element, wherein the second light blocking element is located above the first photodetector and located between the first light blocking element and the third light blocking element.

Preferably, the first light-emitting element is located outside the first light blocking element, and the second light-emitting element is located outside the third light blocking element.

Preferably, the first light-emitting element and the second light-emitting element and the first photodetector are linearly arranged.

Preferably, the second light blocking element is disposed in parallel with the testing element, and the extension of the first and third light blocking elements intersects the testing element.

Preferably, neither the first light blocking element nor the second light blocking element is in contact with the testing element, and the third light blocking element is in contact with the testing element.

Preferably, the second light blocking element is disposed between the first photodetector and the testing element.

In a second aspect of the present invention, the present invention provides a method for reading an assay result on a testing element, providing the foregoing reading apparatus, wherein the apparatus comprising: a first light-emitting element, emitting light and illuminating the corresponding one or more areas of the testing element; a first photodetector, receiving light from one or more corresponding areas of the testing element; a light blocking element, for guiding a path of light emitted from a light emitting element and/or from a testing element, such that light from the testing element is received by or substantially received by the photodetector.

In the present invention, the light emitting element emits light to illuminate the corresponding area of the testing element, which is received by the photodetector after reflection, and then electrical signals that can be detected are formed, so as to determine the test results.

Preferably, the light blocking element comprises a first light blocking element and a second light blocking element, wherein the first light blocking element is located between the first light-emitting element and the first photodetector, such that the lights emitted from the first light-emitting element illuminate to the testing element but not illuminate to the first photodetector.

Preferably, the second light blocking element is located above the first photodetector, such that the second light blocking element guides the light from the testing element to illuminate the first photodetector.

Preferably, the second light blocking element is disposed between the first photodetector and the testing element, to separate one or more areas corresponding to the testing element, or separate one or more areas corresponding to the testing element from the first photodetector, such that the light from the corresponding areas of the testing element can be received by the first photodetector while that from other corresponding areas of the testing element cannot be received by the first photodetector.

Preferably, the second light blocking element is disposed in an area between the testing area and the control area of the testing element, such that the light from the testing area and/or the control area of the testing element can be received by the first photodetector, while the light from the area between the testing area and the control area of the testing element cannot be received by the first photodetector.

Preferably, the second light blocking element is disposed in a reference area of the testing, to separate the testing area from the control area of the testing element, such that the light from the testing area and/or the control area of the testing element can be received by the first photodetector, while the light from the reference area of the testing element cannot be received by the first photodetector.

Preferably, the extension of the first light blocking element intersects the testing element, and the second light blocking element is longitudinally parallel to the testing element.

Preferably, the second light blocking element and the first light blocking element are disposed in a mutually perpendicular form.

Preferably, the apparatus further comprises a third light blocking element, the first photodetector is located between the first light blocking element and the third light blocking element.

Preferably, the second light blocking element is located between the first light blocking element and the third light blocking element, and the second light blocking element covers the first photodetector.

Preferably, the apparatus further comprises a second light-emitting element, and the second light-emitting element is disposed outside the third light blocking element.

Preferably, the first light-emitting element and the first photodetector are linearly arranged, or the first light-emitting element and/or the second light-emitting element are/is linearly arranged with the first photodetector.

Preferably, the light blocking element has a gap that transmits light from the testing element.

Preferably, the gap is formed by providing a certain space between the first light blocking element and the second light blocking element.

Preferably, the gap is a slanted gap such that the light from the testing element is received by the first photodetector through the gap.

Preferably, the first light-emitting element corresponds to the testing area of the testing element, and the second light-emitting element corresponds to the control area of the testing element, so that the first light-emitting element and the second light-emitting element sequentially emit light to illuminate the testing area and the control area of the testing element, and the light is received by the first photodetector through reflection, thereby forming an electrical signal for determining the detection result.

Preferably, the reading apparatus further comprises a fourth light blocking element and a fifth light blocking element, wherein the fourth light blocking element and the fifth light blocking element are respectively located above the first light-emitting element and the second light-emitting element, to cover or partially cover the first light-emitting element and the second light-emitting element.

Preferably, the fourth light blocking element and the fifth light blocking element are respectively located on two sides of the second light blocking element, and are longitudinally parallel with the testing element. When the testing element is fixed to the reading apparatus, the fourth light blocking element and the fifth light blocking are in contact with the testing element to cover the corresponding area of the testing element.

Preferably, the fourth light blocking element covers the area in front of the testing area of the testing element, and blocks the light emitted by the first light-emitting element from illuminating the area in front of the testing area of the testing element.

Preferably, the fifth light blocking element covers the area behind the control area of the testing element, and blocks the light emitted by the second light-emitting element from illuminating the area behind the control area of the testing element.

Preferably, a gap is provided between the fourth light blocking element and the first light blocking element, between the fifth light blocking element and the third light blocking element respectively, to allow the light emitted from the first light-emitting element and the second light-emitting element to illuminate the testing element.

In a third aspect, the present invention provides another reading apparatus for reading an assay result, wherein the apparatus comprising:

a first light-emitting element, emitting light and illuminating the corresponding one or more areas of the testing element; a first photodetector, receiving light from one or more corresponding areas of the testing element; a light blocking element, for guiding a path of light emitted from a light emitting element and/or from a testing element.

Preferably, the light blocking element comprises a first light blocking element and a second light blocking element, the light blocking element separates photodetectors in separate spaces, wherein the first light blocking element is located between the first light-emitting element and the first photodetector, to guide the light emitted from the light emitting element to illuminate one or more areas of the testing element.

Preferably, the second light blocking element allows light from a testing element or light from a specific area to be received by the photodetector.

Preferably, the second light blocking element is located above the first photodetector.

Preferably, the second light blocking element is disposed between the first photodetector and the testing element.

Preferably, the extension of the first light blocking element intersects the testing element, and the second light blocking element is longitudinally parallel to the testing element.

Preferably, the second light blocking element and the first light blocking element are disposed in a mutually perpendicular form.

Preferably, the first light blocking element cooperates with the second light blocking element to guide the light emitted by the light emitting element to illuminate one or more areas of the testing element, and allow the light from the testing element or the light from a specific area of the testing element to be received by the photodetector.

Preferably, the light blocking element has a gap that transmits light from the testing element.

Preferably, the gap is disposed at a position corresponding to a testing area or a control area of the testing element.

Preferably, the gap comprises a first gap and/or a second gap.

Preferably, the first light blocking element has a first gap.

Preferably, the first gap is a slanted gap.

Preferably, the second light blocking element has a second gap.

Preferably, the second gap is in communication with the first gap.

Preferably, the apparatus further comprises a third light blocking element, wherein a second photodetector is disposed outside the third light blocking element.

Preferably, the third light blocking element does not have a gap.

Preferably, the second light blocking element is disposed in a testing area or a control area of the testing element.

Preferably, the apparatus further comprises a second light-emitting element, the first light-emitting element and the second light-emitting element are disposed at a position corresponding to a testing area or a control area of the testing element.

Preferably, there is no light blocking element between the first light-emitting element and the second light-emitting element.

Preferably, a third photodetector is provided between the first light-emitting element and the second light-emitting element.

Preferably, the first light-emitting element and/or the second light-emitting element and/or the third photodetector are linearly arranged.

Preferably, at least one of the first photodetector and the second photodetector is separated by a light blocking element in a separate space.

Preferably, the reading apparatus further comprises a lateral flow testing element, and the testing element comprises a testing area and a control area.

In one preferred embodiment, the present invention provides a reading apparatus for reading an assay result on a testing element, wherein the apparatus comprising:

a first and a second light-emitting elements, emitting light and illuminating one or more corresponding areas of the testing element;

a first and a second photodetectors, receiving light from one or more corresponding areas of the testing element;

a light blocking element, for guiding a path of light emitted from a light emitting element and/or from a testing element, wherein the light blocking element separates at least one photodetector in a separate space.

Preferably, the light blocking element comprises a first light blocking element and a second light blocking element, wherein the first light blocking element is located between the first light-emitting element and the first photodetector, such that the lights emitted from the first light-emitting element illuminate to the testing element but not illuminate to the first photodetector.

Preferably, the second light blocking element is located above the first photodetector, to guide the light from the corresponding area of the testing element to illuminate the first photodetector.

Preferably, the light blocking element has a gap that transmits light from the testing element.

Preferably, the gap is disposed at a position corresponding to a testing area or a control area of the testing element.

Preferably, the gap comprises a first gap and/or a second gap.

Preferably, the first light blocking element has a first gap.

Preferably, the first gap is a slanted gap.

Preferably, the second light blocking element has a second gap.

Preferably, the second gap is in communication with the first gap.

Preferably, the light blocking element further comprises a third light blocking element for separating the two photodetectors and the third light blocking element does not have a gap.

Preferably, the two photodetectors are separated by a shared third light blocking element, or the two photodetectors are separated by two third light blocking elements that are separated from each other.

Preferably, the two third light blocking elements that separate from each other have a longitudinal parallel structure.

Preferably, the first photodetector and the second photodetector are linearly arranged.

Preferably, the first light-emitting element and the second light-emitting element are disposed at a position corresponding to a testing area or a control area of the testing element respectively.

Preferably, there is no light blocking element between the first light-emitting element and the second light-emitting element.

Preferably, a third photodetector is provided between the first light-emitting element and the second light-emitting element.

Preferably, the first light-emitting element, the second light-emitting element and/or the third photodetector are linearly arranged.

In a fourth aspect herein, the present invention provides another method for reading an assay result on a testing element, providing the foregoing reading apparatus, wherein the apparatus comprising: a first light-emitting element, emitting light and illuminating the corresponding one or more areas of the testing element; a first photodetector, receiving light from one or more corresponding areas of the testing element; a light blocking element, for guiding a path of light emitted from a light emitting element and/or from a testing element.

Preferably, the light blocking element separates at least one photodetector in a separate space such that the light from a specific area of the testing element enters the first photodetector.

Preferably, the light blocking element comprises a first light blocking element and a second light blocking element, wherein the first light blocking element is located between the first light-emitting element and the first photodetector, to guide the light emitted from the light emitting element to illuminate one or more areas of the testing element.

Preferably, the second light blocking element is located above the first photodetector, such that the light from the testing element or light from a specific area of the test element is received by the first photodetector.

Preferably, the light blocking element has a gap that transmits light from the testing element, such that the light from a specific area of the testing element enters the first photodetector through the gap.

Preferably, the gap is disposed at a position corresponding to a testing area or a control area of the testing element, such that the light from a testing area or a control area of the testing element enters the first photodetector through the gap.

Preferably, the gap comprises a first gap and/or a second gap.

Preferably, the first light blocking element has a first gap.

Preferably, the first gap is a slanted gap.

Preferably, the second light blocking element has a second gap.

Preferably, the second gap is in communication with the first gap.

Preferably, the apparatus further comprises a third light blocking element, wherein a second photodetector is disposed outside the third light blocking element.

Preferably, the third light blocking element does not have a gap.

Preferably, the second light blocking element is disposed in a testing area or a control area of the testing element.

Preferably, the apparatus further comprises a second light-emitting element, the first light-emitting element and the second light-emitting element are disposed at a position corresponding to a testing area or a control area of the testing element.

Preferably, there is no light blocking element between the first light-emitting element and the second light-emitting element.

Preferably, a third photodetector is provided between the first light-emitting element and the second light-emitting element.

Preferably, the first light-emitting element and/or the second light-emitting element and/or the third photodetector are linearly arranged.

Preferably, the first light-emitting element and the second light-emitting element sequentially emit light, and the light illuminates the testing area and the control area of the testing element, and enters the first photodetector and the second photodetector after reflection, to form an electrical signal for determining the detection result, which is used for determination of test results.

The present invention can achieve the following beneficial effects:

First, the reading apparatus of the present invention guides or changes the light path through the light blocking element, providing a better optical path between the light emitting element and the photodetector. The reading apparatus of the present invention is compact in structure, ensuring adequate and effective use of the optical path signals. The reading apparatus of the present invention allows light from as specific area of the testing element to be received by the photodetector and blocks invalid light from unrelated areas from entering the photodetector, thereby enhancing the accuracy and sensitivity of detection.

Second, a photodetector is provided between light emitting elements for reading apparatus of the present invention for initial calibration, which realizes dimming and calibration before use, hereby ensuring the accuracy of the detection result.

BRIEF DESCRIPTION OF THE DRAWINGS

FIGS. 9A and 9B are a partially enlarged schematic view of FIG. 8, in which FIG. 9A is a top view and FIG. 9B is a front view.

Figure 1:
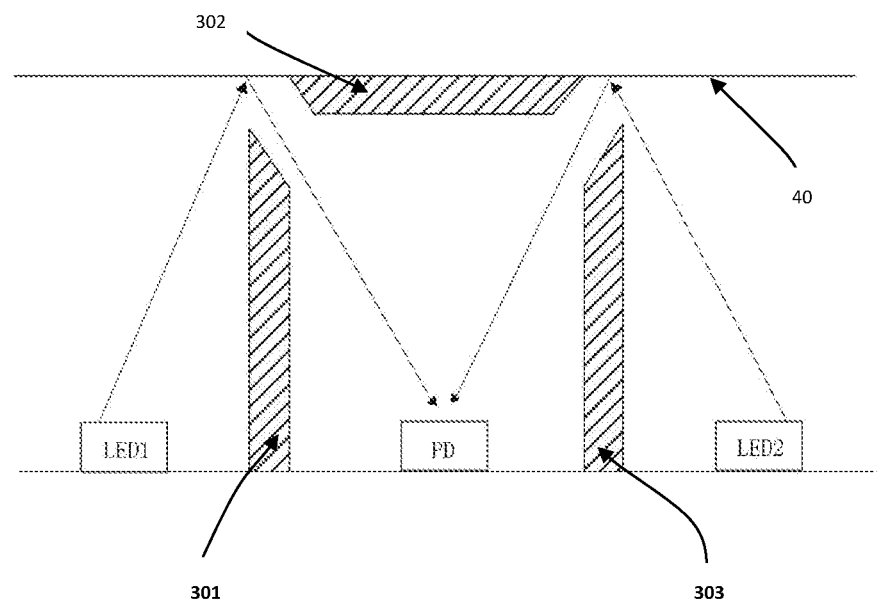
FIG. 1 is a schematic view of the principle of a reading apparatus according to a particular embodiment of the present invention.

NOTES 101 first light-emitting element,
102 second light-emitting element,
201 first photodetector,
202 second photodetector,
203 third photodetector,
30 light blocking element,
301 first light blocking element,
302 second light blocking element,
303 third light blocking element,
304 fourth light blocking element,
305 fifth light blocking element,
3011 first light blocking element,
3021 second light blocking element,
3031 third light blocking element,
3041 fourth light blocking element,
3051 fifth light blocking element,
3061 sixth light blocking element,
3071 seventh light blocking element,
3081 eighth light blocking element,
3091 ninth light blocking element,
3101 tenth light blocking element,
40 testing element,
401 sample absorption area,
402 reagent area,
403 testing area,
404 reference area,
405 control area,
406 water absorption area,
407 and 408 areas near the testing area,
409 and 410 areas near the control area,
50 gap,
501 first gap,
502 second gap,
503 third gap,
504 fourth gap,
5011 first gap,
5012 second gap,
60 base board,
70 base frame,
701 detection window,
702 slot,
703 tray,
704 protrusion,
7031 groove, 7041 protrusion,
80 upper casing,
90 lower casing,
100 cover body,
110 sample application stick,
120 front conduction electrode,
130 display,
140 power supply element,
150 buzzer.

DETAILED DESCRIPTION

The structures involved in the present invention or technical terms used therein will be further described below. These descriptions are merely illustrative of how the present invention is achieved by examples, and are not intended to limit the present invention in any way.

Detection

Detection means to assay or test the presence or absence of a substance or material, including but not limited to chemical substances, organic compounds, inorganic compounds, metabolic products, medicines or drug metabolites, organic tissues or metabolites of organic tissues, nucleic acids, proteins or polymers. Additionally, detection means to test the quantity of a substance or material. Furthermore, assay also means immunodetection, chemical detection, enzyme detection, etc.

Samples

The detection apparatus provided in the invention can be used to detect samples including biological liquid (such as case liquid or clinical samples). The liquid sample or fluid sample can come from solid or semi-solid samples, including excreta, biological tissues and food samples, and these solid or semi-solid samples can be converted to liquid samples by using any suitable methods such as mixing, crushing, macerating, incubating, dissolving or digesting the solid samples in a suitable solution (such as water, phosphate solution or other buffer solutions) with the enzymolysis. "Biological samples" comprise samples from animals, plants and food, such as urine, saliva, blood and its components, spinal fluids, vaginal secretion, sperms, excrement, sweat, secreta, tissues, organs, tumors, cultures of tissues and organs, cell cultures and media from human or animals. The preferred biological sample is urine; food samples comprise food processed substances, final products, meat, cheese, liquor, milk and drinking water; and plant samples comprise samples from any plants, plant tissues, plant cell cultures and media. "Environmental samples" come from the environment (such as liquid samples coming from lake or other water bodies, sewage samples, soil samples, underground water, sea water and effluent samples), and can also comprise waste water or other sewage water.

Any analyte can be detected by using this apparatus herein and a suitable testing element. Preferably, the apparatus in the present invention is used for detection of early pregnancy. The preferred samples are urine samples.

Analyte

The analytes detected by this invention include but not limited to creatinine, bilirubin, nitrite, (non-specific) proteins, hormones (such as human chorionic gonadotropin, progesterone hormone, follicle-stimulating hormone), blood, leucocytes, sugar, heavy metals or toxins, bacterial substances (such as proteins or sugar substances against specific bacteria, such as *Escherichia coli* 0157:H7, *Staphylococcus, Salmonella, Fusobacterium, Campylobacter, L. monocytogenes, Vibrio* or *Bacillus cereus*) and substances relevant with the physiological features in the urine sample, such as pH and specific gravity.

In addition, the apparatus in the present invention can be used to detect drugs of abuse, such as cocaine, amphetamine AMP, methamphetamine MET, barbiturate BAR, sedatives, lysergic acid diethylamide (LSD), inhibitors (downers, goofballs, barbs, blue devils, yellow jackets, methaqualone), tricyclic antidepressants (TCA), opiates, anxiolytics and sedative hypnotics, etc. The detection apparatus provided in this invention can also be used to detect medicines that are easy to overdose for the medical purpose, such as tricyclic antidepressants (imipramine or analogues) and acetaminophen. These medicines will be resolved into different micromolecular substances after being absorbed by human body, and these micromolecular substances will exist in blood, urine, saliva, sweat and other body fluids or in some of the body fluids.

For any other clinical urine chemical analysis, the detection can be made by combining the lateral flow detection form and the apparatus provided in this invention.

In one embodiment, the analyte is any detectable substance. In one embodiment, the analyte comprises a labeled reagent, for example, a labeled conjugate that exhibits binding affinity on the target analyte or analogues of target analyte.

In one embodiment, the analyte comprises a direct label, for example, a dye or a gold particle. The accumulation of substances marked in this manner may produce a detectable effect on the amount of light reflected or transmitted by the testing area.

In a preferred embodiment, the analyte is HCG or LH for detecting pregnancy or ovulation.

Testing Element

Various testing elements can be applied to this invention by combination. In some embodiments herein, the preferred testing element is a test strip. The test strip may be in various forms, for example, the forms of immunoassay or chemical test, used to detect analytes in samples, such as drugs or relevant metabolites indicating physical conditions. In some forms, the test strip is a water absorbent material having a sample applying area, a reagent area and a testing area. Samples are added to the sample applying area, and flow to the reagent area under the capillary action. In the reagent area, samples dissolve the reagent and mix with it to detect analyte (if there is analyte in samples). At this time, samples with reagents continue to flow to the testing area. Other reagents, for to example, molecules that specifically bind to the analyte, are fixed in the area, or bind a reagent in the reagent area.

In one particular embodiment, the test strip comprises a labeled specific binding reagent used for the analyte that is usually disposed in a reagent area of a test strip, and a non-labeled specific binding reagent that can be specifically binding to the same analyte. The reagent is immobilized in a testing area at the downstream of the labeled specific binding reagent. When the liquid sample containing the analyte is applied to the test strip, the liquid sample flows on the test strip, and the analyte is bound with the marked specific binding reagent, to form a complex, wherein the labeled substance is colored. The composite is further mobilized to the testing element and bind with a non-labeled specific binding reagent immobilized in the testing area to form another complex such that the analyte is detected in the testing area. In particular, the detection contains the accumulation of the labeled substance in the testing area. The presence of the analyte in the sample tends to cause accumulation of the labeled substance.

The test strip may comprise a variety of materials for the transfer of liquid samples. One of the materials may be covered on another material, for example, a filter paper covers a nitrocellulose membrane. One area of the test strip can use one or more kinds of materials, and another area can use one more kinds of different materials. The test strip can be adhered to a support or a hard surface to increase the strength of the test strip.

During the detection process, an analyte is detected by a signal generating system, for example, one or more compositions of signal generating systems are immobilized on the analyte testing area of the test strip using one or more enzymes that specifically react with the analyte according to the method of immobilizing the specific binding substance on the test strip as described above. The signal generating substance may be on a sample applying area, a reagent area, or a testing area, or the whole test strip, which can be filled with one or more materials of the test strip. In particular, the detection preferably includes the accumulation of labeled substance, usually the accumulation of labeled substance in the testing area. The labeled substance may be colored particles such as an enzyme, a radioisotope tracer, fluorescein, colloidal gold, or color latex, etc.

Various areas of the test strip can be arranged in the following manner: a sample applying area, a reagent area, a testing area, and a control area, to determine if the sample is an adulteration area, a liquid sample absorption area. The control area is located behind the testing area. All areas may be arranged on a test paper using one material only. Each area may be in direct contact with the liquid sample, or different areas may be arranged in the direction in which the liquid sample flows, and the end of each area is connected to and overlapped with the front end of another area. The material used may be a material having a good water absorption property, for example, a filter paper, a glass fiber or a nitrocellulose membrane, or other forms.

The testing element applied to the present invention may be a lateral flow test strip. The structure and detection principle of these test strips are well known in the art to those skilled in the art, for example, forms disclosed in U.S. Pat. Nos. 6,156,271, 5,504,013 and EP728309, etc. The testing element may comprise a plurality of areas, for example, a sample collection area, a labeling area, a testing area, and a water absorption area. The sample collection area includes a sample receiving pad, the labeling area includes a labeling pad, and the water absorption area may include an absorbent pad, wherein the testing area includes essential chemical substances that can detect the presence or absence of an analyte, for example, an immunological reagent or an enzyme chemical reagent. Of course, a control area may be included at the downstream of the testing area. Generally, the control area and the testing area have horizontal lines, which are detection lines or control lines. Usually the test strips have dry chemical reagent components, for example, immobilized antibody or other reagents. When a liquid sample is encountered, the liquid flows along the test strip with capillary action, and the dry reagent component is dissolved in the liquid as it flows to the next area to have reactions with dry reagent in the area, to complete the necessary detection. The liquid flow mainly depends on capillary action.

Figure 5:
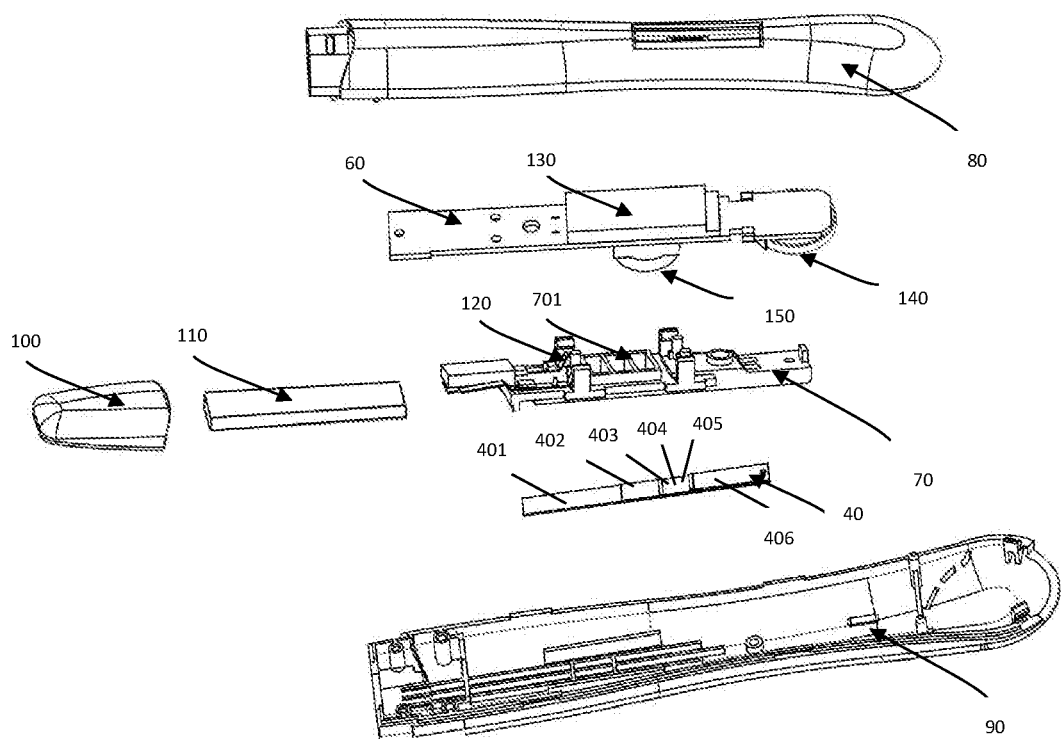
FIG. 5 is an exploded view of a reading apparatus according to a particular embodiment of the present invention.
Figure 13:
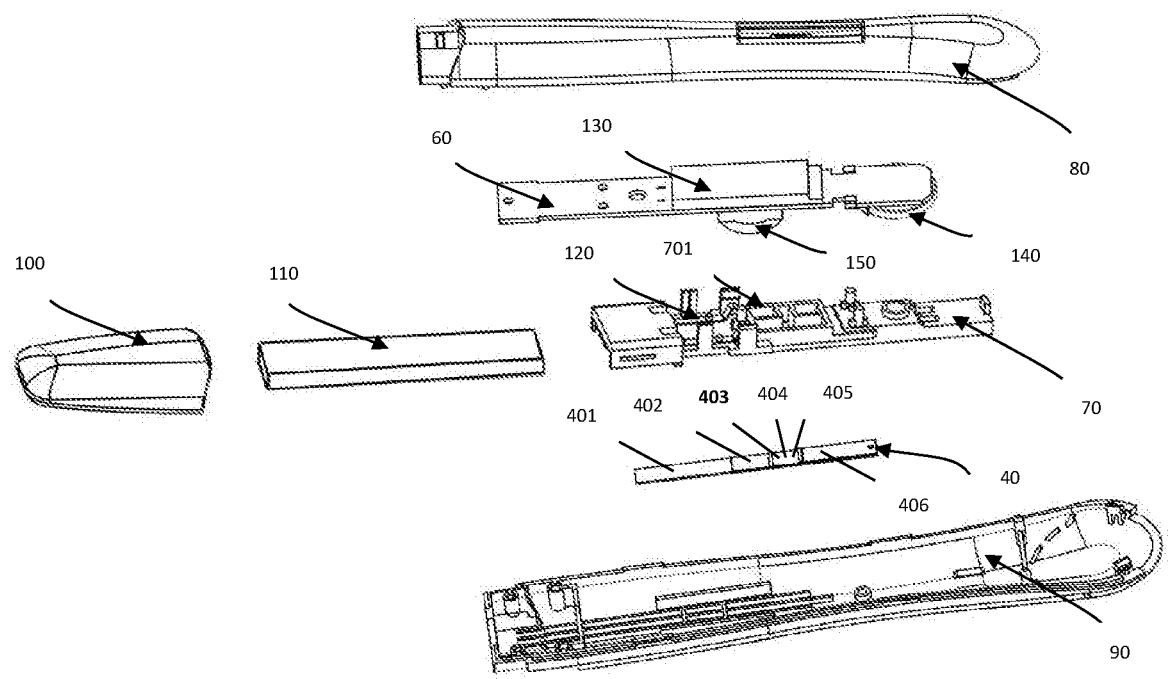
FIG. 13 is an exploded view of a reading apparatus according to another particular embodiment of the present invention.

In one particular embodiment of the present invention, as shown in FIG. 5 and FIG. 13, the testing element 40 has a sample absorption area 401, a reagent area 402, a testing area 403, a reference area 404, a control area 405, and a water absorption area 406. The testing area 403 is an area in which a light signal is formed in the testing element, and is a stacking area or a storage area of a labeled substance, for example, a particulate colored binding reagent, representing the presence or absence of the analyte. Of course, in the absence of the analyte, some analyses such as substitution analysis may form a signal. The control area 405 is another area on the testing element capable of forming an optical signal for indicating whether the detection is performed correctly and/or whether the binding actually has an effect, regardless of the presence or absence of the analyte. The reference area 404 is an area between the testing area and the control area and is an area that only forms a "background" signal, for example, the signal can be used to calibrate the reading apparatus and/or provide a reference signal for the test signal. A reference area may not be provided between the testing area and the control area.

In one particular embodiment of the present invention, the testing area 403 and/or the control area 405 of the testing element correspond to the light emitting element of the reading apparatus of the present invention, and the light emitted by the light emitting element emits the testing area 403 or the control area 405 of the testing element, and the light reflected from the area emits the photodetector, thereby producing an electrical signal that can be detected, indicating the amount of analyte in the area.

In some other particular embodiments, a reading apparatus provided by the present invention comprises a light blocking element as shown in FIG. 1. The light blocking element includes a first light blocking element 301, a second light blocking element 302, and a third light blocking element 303, wherein, the second light blocking element 302 is located between the photodetector 201 and the testing element 40 such that part of the light from the testing element is blocked by the second light blocking element 302, thereby preventing part of the light from being received by the photodetector 201. In one embodiment, for example, the reference area between the testing area and the control area in FIG. 1 is blocked by the second light blocking element 302, such that the light in the reference area is not received by the photodetector, thereby reducing interference. In the following, the structure and working principle of the reading apparatus will be specifically described.

Figure 8:
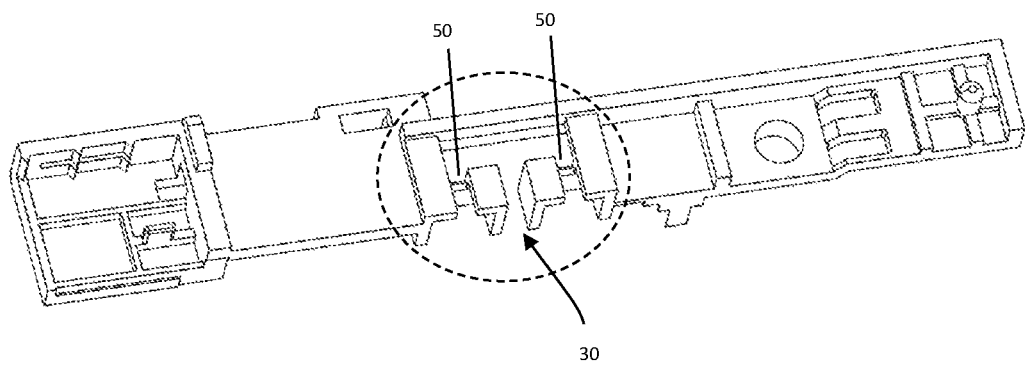
FIG. 8 is a schematic cross-sectional view of a reading apparatus according to another particular embodiment of the present invention.
Figure 9A:
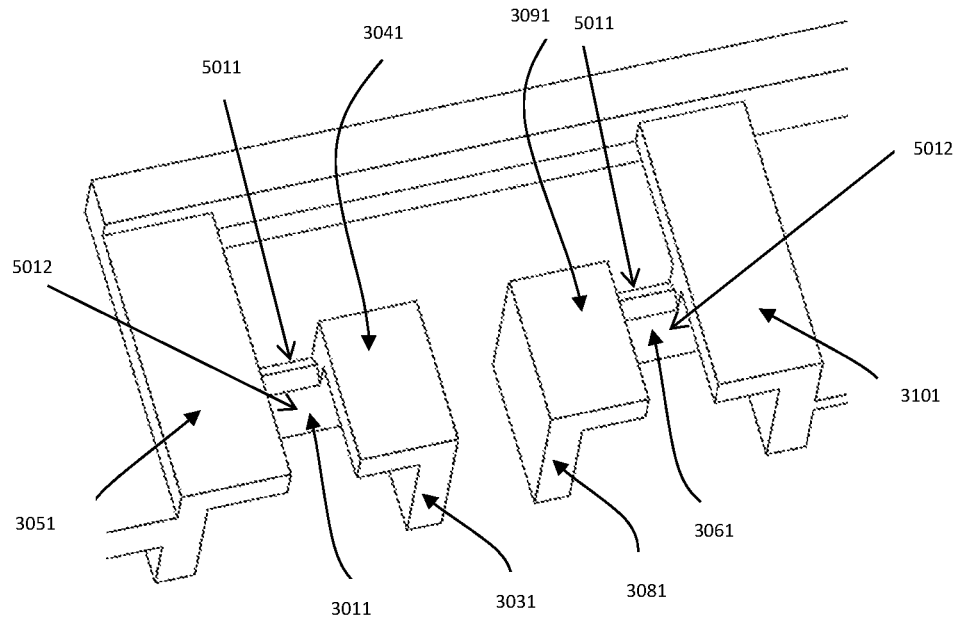
Figure 9B:
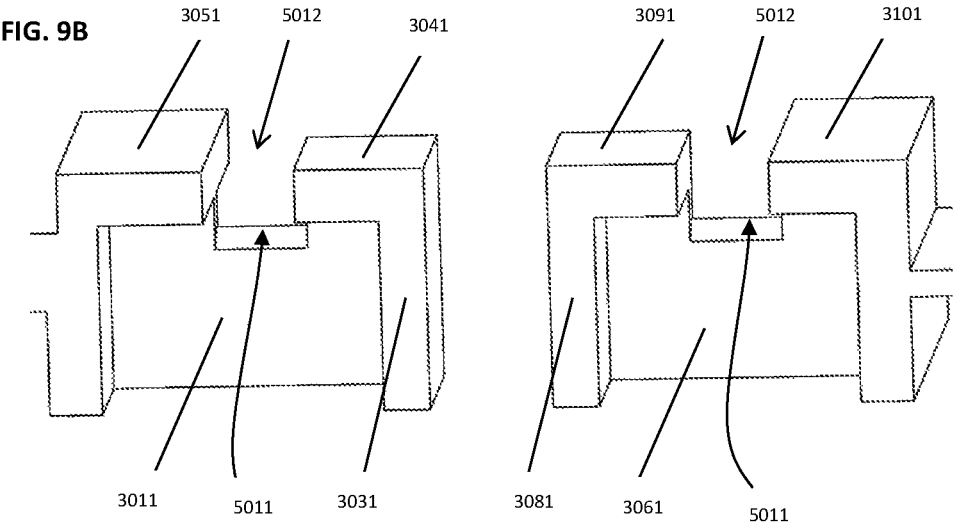

In some other particular embodiments, another reading apparatus provided by the present invention comprises a light blocking element 30 such as shown in FIG. 8 and FIG. 9. The light blocking element 30 separates the photodetector from the light emitting element, thereby avoiding the light emitted from the light emitting element from entering the photodetector directly and guiding the light from the testing element to enter the photodetector or to be substantially received by the photodetector. Further, the light blocking element 30 blocks the light from one or more corresponding areas of the testing element 40, and guides the light of the light emitting element to the one or more corresponding areas of the testing element, thereby guiding the light from another area or more areas of the testing element to enter the photodetector, preferably the light blocking element guides the light from the testing area and control area of the testing element to enter the photodetector, or to be substantially received by the photodetector. In the following, the structure and working principle of the reading apparatus will be specifically described.

Light Emitting Element and Photodetector

The light emitting element and the photodetector constitute an optical detection system that detects the accumulation of the analyte on the testing element. Wherein, the light emitting element is used to emit light and illuminate one or more corresponding areas of the testing element. A plurality of light sources capable of emitting light is suitable as the light emitting element. In one particular embodiment, the light emitting element is a light emitting diode, for example, an LED lamp. The photodetector is used to detect the light irradiated thereon and convert it into a detectable electrical signal, which is proportional to the amount of the labeled substance accumulated on the testing element, the light, like reflected light is formed by the light emitted by the light emitting element after reflection by the testing element, or can be thought of as light from the testing element, although the light is substantially from the light emitting element. In one particular embodiment, the photodetector is a photodiode (PD detector). Appropriate light emitting elements and photodetectors are well known to those skilled in the art.

In one embodiment, the present invention provides a reading apparatus, as shown in FIG. 1-FIG. 5. The reading apparatus comprises at least one light emitting element and at least one photodetector. Wherein, the at least one light emitting element includes a first light-emitting element 101, and the light emitted by the first light-emitting element 101 illuminates to one or more corresponding areas of the testing element 40; the at least one photodetector includes a first photodetector 201, and the light emitted by the light emitting element is received by the photodetector after reflected by the corresponding area of the testing element 40. In one preferred embodiment, the first photodetector 201 is disposed in an area between the testing area and the control area of the corresponding testing element, or the first photodetector 201 is disposed in an area corresponding to the reference area of the testing element. In one preferred embodiment, the first light-emitting element 101 and the first photodetector 201 are linearly arranged.

Figure 4:
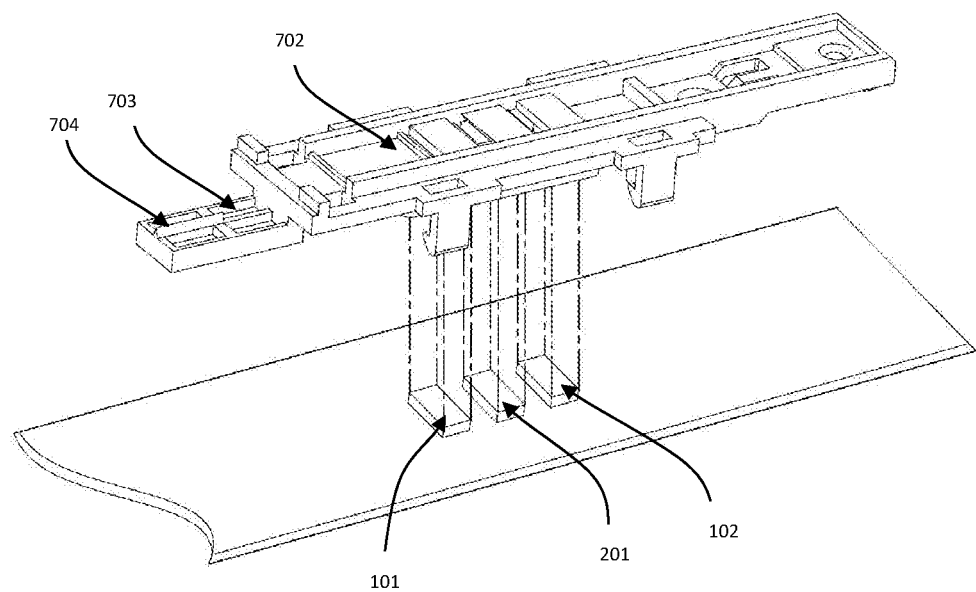
FIG. 4 is a top schematic view of a reading apparatus according to a particular embodiment of the present invention.

In some preferred embodiments, the reading apparatus comprises at least two light emitting elements and at least one photodetector 201, wherein the at least two light emitting elements include a first light-emitting element 101 and a second light-emitting element 102, the light emitted by the first light-emitting element 101 and the second light-emitting element 102 illuminates one or more corresponding areas of the testing element 40, and is received by the first photodetector 201 after reflection. The first light-emitting element 101 and the second light-emitting element share the first photodetector 201. In a preferred embodiment, the first photodetector 201 is located between the first light-emitting element 101 and the second light-emitting element 102, and can sequentially receive light emitted by at least two spatially separated areas of the testing element (FIG. 1 and FIG. 4). In one preferred embodiment, the light emitted by the first light-emitting element 101 and the second light-emitting element 102 respectively illuminates to the testing area 403 and the control area 405 of the testing element, and the first photodetector 201 is located between the first light-emitting element 101 and the second light-emitting element 102, to receive the light from the testing area 403 and the control area 405 of the testing element sequentially. In one preferred embodiment, the first light-emitting element 101 and/or the second light-emitting element 102 and the first photodetector 201 are linearly arranged. Preferably, the two light emitting elements emit light sequentially, that is, emitting light at different times, with a difference in time. Preferably, the light emitted by the two light emitting elements has the same wavelength.

For the linear arrangement herein, preferably the light emitting element and the photodetector are on the same line, but they are not limited in this way. The light emitting element and the photodetector can be staggered from each other. The test strip generally has a certain width and the light received from the light emitting element has a certain area, and the light reflected or emitted from the test strip also has a certain area, actually a light beam or light area with a three-dimensional shape is feasible as long as the photodetector is within these light beam or light areas with three-dimensional shapes. Therefore, a slight offset between the light emitting element and the photodetector is also a solution of the present invention.

In another particular embodiment, the present invention provides a reading apparatus, as shown in FIG. 7 to FIG. 13, the reading apparatus comprises a first light-emitting element 101, at least two photodetectors, including a first photodetector 201 and a second photodetector 202. The light emitted by the first light-emitting element 101 illuminates to one or more corresponding areas of the testing element 40, and the light is received by the first photodetector 201 and the second photodetector 202 after reflection in the corresponding areas of the testing element 40. In one preferred embodiment, the first photodetector 201 and the second photodetector 202 are disposed at positions corresponding to the testing area and the control area of the testing element, to receive the light from the testing area and the control area of the testing element respectively. In one preferred embodiment, the first photodetector 201 and the second photodetector 202 are linearly arranged, and the first light-emitting element 101 is located opposite the first photodetector 201 and the second photodetector 202, and is disposed in parallel with the first photodetector 201 and the second photodetector 202, that is, the first photodetector 201 and the second photodetector 202 share a light emitting element. In one preferred embodiment, the first light-emitting element 101, the first photodetector 201, and the second photodetector 202 are arranged in a "品" shape.

Figure 6:
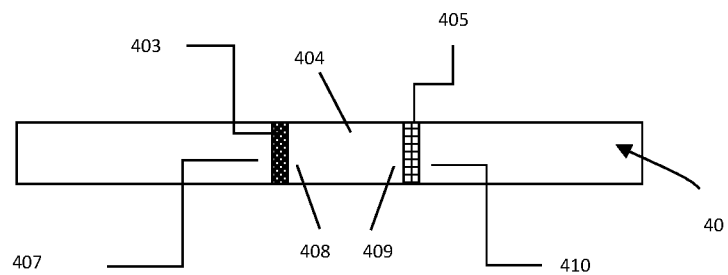
FIG. 6 is a schematic view of a testing element according to a particular embodiment of the present invention.
Figure 10:
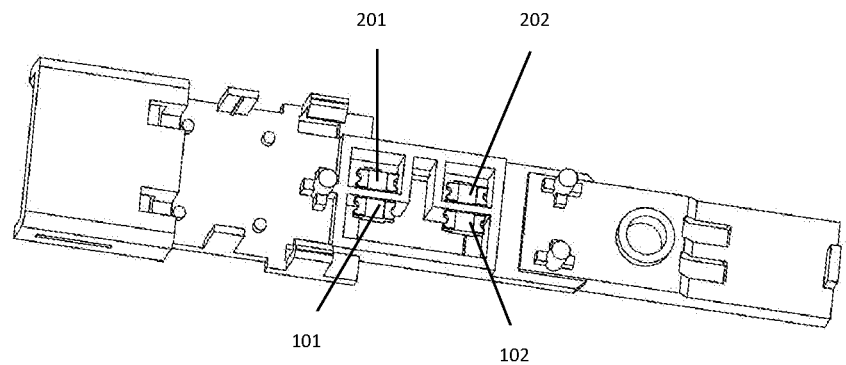
FIG. 10 is a bottom schematic view of a reading apparatus according to another particular embodiment of the present invention.

In some preferred embodiments, the reading apparatus comprises at least two light emitting elements and at least two photodetectors, wherein the at least two light emitting elements include a first light-emitting element 101 and a second light-emitting element 102. The light emitted by the first light-emitting element 101 and the second light-emitting element 102 respectively illuminate the one or more corresponding areas of the testing element 40, and the light is received by the first photodetector 201 and the second photodetector 202 respectively after reflection (FIG. 10). In one preferred embodiment, the first photodetector 201 is disposed corresponding to the first light-emitting element 101, and the second photodetector 202 is disposed corresponding to the second light-emitting element 102. The first photodetector 201 and the second photodetector 202 may respectively receive light from at least two spatially separated areas of the testing element. In one preferred embodiment, the first light-emitting element 101 is located opposite the first photodetector 201, and is linearly arranged with the first photodetector 201, and the second light-emitting element 102 is located opposite the second photodetector 202 and is linearly arranged with the second photodetector 202. In one preferred embodiment, the light emitted by the first light-emitting element 101 illuminates the testing area of the testing element 40 and the areas 407 and 408 (FIG. 6) near the testing area, for example, illuminating the testing area 403 and/or part of the reference area 404 and/or part of the reagent area 402, the light emitted by the second light-emitting element 102 illuminates the control area 405 of the testing element and the areas 409 and 410 (FIG. 6) near the control area, for example, the control area 405 of the testing element and/or part of the reference area 404 and/or part of the water absorption area 406. The first photodetector 201 receives light from the testing area 403 of the testing element and the area near the testing area, and the second photodetector 202 receives light from the control area 405 of the testing element and the area near the control area. In one preferred embodiment, the light emitted by the first light-emitting element 101 illuminates the testing area 403 of the testing element 40, and the light emitted by the second light-emitting element 102 illuminates the control area 405 of the testing element, and the first photodetector 201 and the second photodetector 202 respectively receive the light from the testing area 403 and the control area 405 of the testing element. The light emitting elements correspond to the photodetector one-to-one, to accurately reflect the optical information of each area of the testing element, ensuring the detection accuracy and sensitivity. In one preferred embodiment, the first light-emitting element 101 and the second light-emitting element 102 are linearly arranged, and the first photodetector 201 and the second photodetector 202 are linearly arranged. Preferably, the two light emitting elements sequentially emit light, that is, the emitted light has a difference in time, forming a luminous time difference. Preferably, the energy of the light emitted by the two light emitting elements is uniform.

Figure 11:
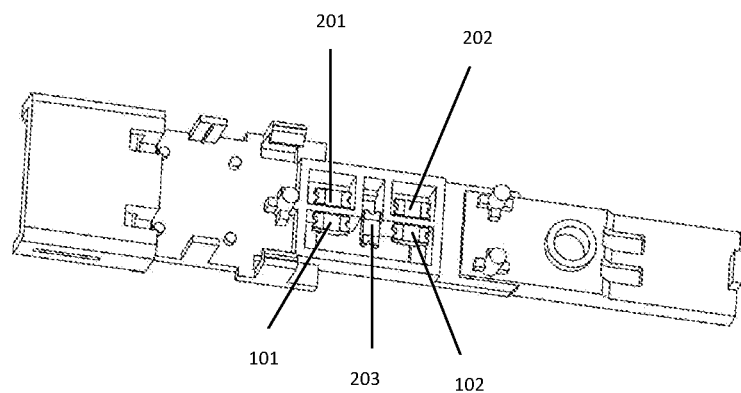
FIG. 11 is a bottom schematic view of a reading apparatus according to another particular embodiment of the present invention.
Figure 12:
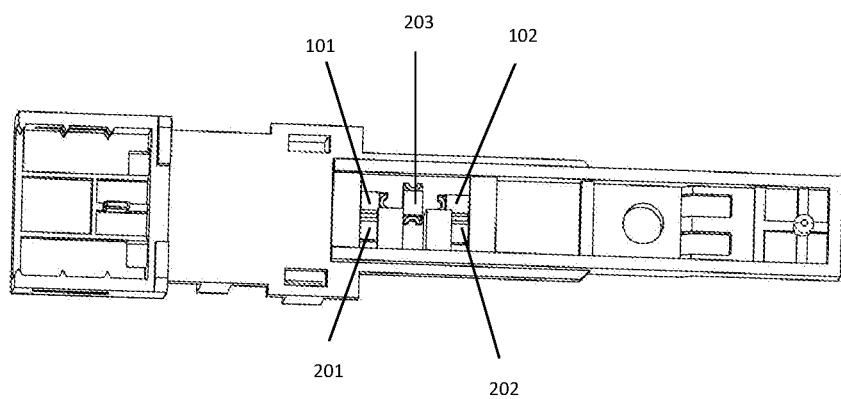
FIG. 12 is a top schematic view of the reading apparatus of FIG. 11.

In some preferred embodiments, the reading apparatus comprises at least two light emitting elements and at least three photodetectors, wherein the at least two light emitting elements include a first light-emitting element 101 and a second light-emitting element 102. The light emitted by the first light-emitting element 101 and the second light-emitting element 102 respectively illuminate one or more corresponding areas of the testing element 40, and the light is respectively received by the first photodetector 201 and the second photodetector 202 after reflection. The third photodetector 203 is used for initial calibration or dimming for the electronic reading apparatus of the present invention prior to use (FIG. 11 and FIG. 12).

In one preferred embodiment, the first photodetector 201 is disposed corresponding to the first light-emitting element 101, and the second photodetector 202 is disposed corresponding to the second light-emitting element 102, and the first light-emitting element 101 and the second light-emitting element 102 are linearly arranged, and the first photodetector 201 and the second photodetector 202 are linearly arranged, and a third photodetector 203 is provided between the first light-emitting element 101 and the second light-emitting element 102. In one preferred embodiment, the third photodetector 203 is located between the first light-emitting element 101 and the second light-emitting element 102. In one preferred embodiment, the third photodetector 203 is located between the first light-emitting element 101 and the second light-emitting element 102 and is linearly arranged with the first light-emitting element 101 and the second light-emitting element 102.

For the above linear arrangement, preferably, the first light-emitting element 101 and the second light-emitting element 102 are located on the same straight line, the first photodetector 201 and the second photodetector 202 are located on the same straight line, or, the first light-emitting element 101 and the first photodetector 201 are located on the same straight line, or the second light-emitting element 102 and the second photodetector 202 are located on the same straight line, or, the first light-emitting element 101, the second light-emitting element 102 and the third photodetector 203 are located on the same straight line, but it does not mean that they are on the same straight line only. Two light emitting elements, and/or two photodetectors, and/or the first light-emitting element 101 and the first photodetector 201, and/or the second light-emitting element 201 and the second photodetector 202, and/or the first light-emitting element 101, the second light-emitting element 102 and the third photodetector 203 may be mutually staggered, for example, the first light-emitting element 101, the second light-emitting element 102 and the third photodetector 203 may be arranged in a "品" shape, and a slight offset of position between the light emitting element and/or the photodetector is also a solution of the present invention.

Light Blocking Element

In some preferred embodiments, the light emitted from the light emitting element emits to a specific area of the testing element, and enters the photodetector after reflected by the testing element. In this case, the light emitting element and the photodetector are usually disposed on the same side of the testing element, therefore, in some embodiments, it is required to provide a light blocking element 30 that allows light from the testing element to be received by the photodetector. On one hand, the light blocking element 30 is used to prevent light from the light emitting element from directly entering the photodetector, and on the other hand, to allow the light from a specific area of the testing element to be received by the photodetector, while block the light in the other areas from being substantially received by the photodetector. Therefore, a light blocking element is provided to change the path of the light emitted from the light emitting element and/or from the testing element, such that the light from the light emitting element emits to one or more corresponding areas of the testing element and the light from one or more corresponding areas of the testing element is received by or substantially received by the photodetector. The distance is related to the distance between the light path and the light emitting element and the testing element, between the light blocking element and the light emitting element, and the height or width of the light blocking element. Generally, it is desired that the light emitted from the light emitting element illuminates the corresponding areas of the testing element as much as possible, but not illuminates other regions unrelated to the detection result, or it is not desirable that the light emitted from the light emitting element is directly received by the photodetector. In this case, generally a light blocking element is provided to prevent the light emitted from the light emitting element from being received by the photodetector. Although the interference is reduced by this way, if the light from the testing element, especially the light not from the target area is not received by the photodetector, it will further reduce the interference of the invalid light on the photodetector, making detection results more sensitive and reliable.

When the light emitted by the light emitting element illuminate the test strip 40, of course, it is desirable to illuminate the testing area on the test strip. For example, a substance, such as an antibody, is already treated on the testing area previously, which has an accumulation of color particulate matter, thereby causing change in the light emitted by the area, and it is hoped that these changes will be received by the photodetector as much as possible, so that these optical changes can be more sensitively reflected, making the test results more accurate. However, at this time, the light emitted by the light emitting element can not only illuminate a specific area, for example, testing area 403, but also can illuminate areas other than the testing area, for example, a reference area 404 between testing area 403 and control area 405, and areas 407 and 408 near the testing area. The light from areas other than the testing area may also illuminate the photodetector, while these lights do not reflect the change of light of the testing area, which belong to interference light. If the interference light is received by the photodetector, it will cause interference to normal light, and it is unable to sensitively identify the change of the testing area, resulting in inaccuracy of the test results. In the prevent invention, a light blocking element is used to block the interference light from the testing area from being received by the photodetector, such that the light from a specific area is received by the photodetector as much as possible, thus improving the sensitivity of the detection.

In some embodiments, the light blocking element 30 is used to guide the path of the light emitted by the light emitting element and/or the light from the testing element, such that the light emitted by the light emitting element illuminates a specific area of the testing element or the light from the testing element (e.g. a specific area) is received by the photodetector as much as possible. The material of the light blocking element 30 should be able to block light, preferably, the light blocking element 30 is an optical baffle (for example, the opaque part that cannot transmit spectra). Suitable materials include deep black, dark black or black synthetic plastic resin, etc., for example, PPO (polyphenylene oxide).

In some embodiments, the light blocking element 30 separates at least one photodetector in a separate space. The separate space means that the separated photodetector is enclosed in a relatively closed space with respect to the light emitting element, the testing element and the other photodetector, such that some light outside the space cannot enter the space. Specifically, the photodetector does not contact the light emitting element, such that the light emitted by the light emitting element cannot directly enter the photodetector. The photodetector does not contact with a part of the testing element or the testing element, such that the light from a part of the testing element or the testing element cannot enter the photodetector, and the photodetector is not in contact with another photodetector, such that the light entering the relatively closed space cannot be received by another photodetector.

In one particular embodiment, the present invention provides a reading apparatus comprising a first light-emitting element 101, a first photodetector 201 and a light blocking element. The light blocking element includes a first light blocking element 301 and a second light blocking element 302, wherein the first light blocking element 301 guides the light emitted from the light emitting element to illuminate one or more areas of the testing element, and the second light blocking element 302 allows the light from the testing element or light from a specific area of the test element to be received by the first photodetector 201. In some preferred embodiments, the first light blocking element 301 and the second light blocking element 302 cooperate to guide the light emitted by the light emitting element to illuminate one or more areas of the testing element, such that the light from the testing element or light from a specific area of the test element is received by the first photodetector 201 (FIG. 1).

Figure 2:
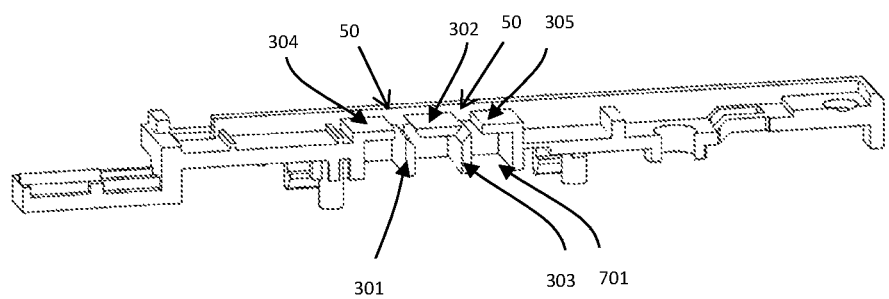
FIG. 2 is a schematic longitudinal sectional view of a reading apparatus according to a particular embodiment of the present invention.
Figure 3:
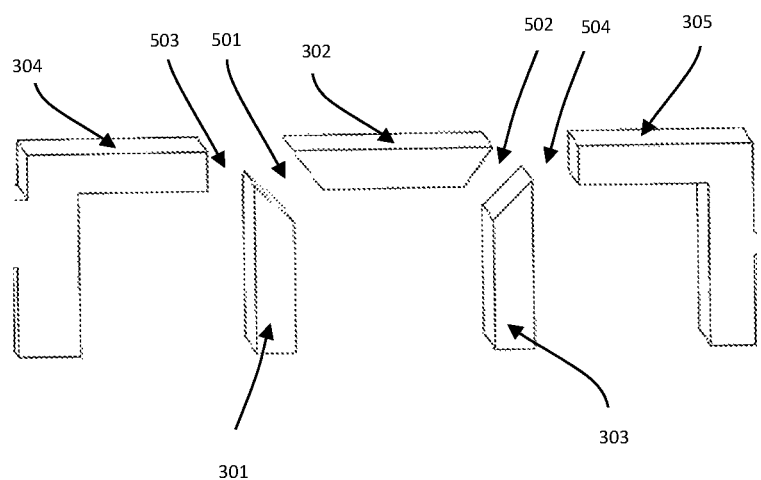
FIG. 3 is a partially enlarged schematic view of a reading apparatus according to a particular embodiment of the present invention.

In one preferred embodiment, the first light blocking element 301 is disposed corresponding to the location where the first light-emitting element 101 and first photodetector 201 are and is located between the first light-emitting element 101 and the first photodetector 201, to separate the first light-emitting element 101 from the first photodetector 201, and guide the light emitted from the first light-emitting element 101 to illuminate the testing element 40 without illuminating the first photodetector 201. In one preferred embodiment, as shown in FIGS. 2 and 3, the first light-emitting element 101 and the first photodetector 201 are respectively located on the left and right sides of the first light blocking element 301, such that the first light blocking element 301 separates the first light-emitting element 101 from the first photodetector 102. In another preferred embodiment, as shown in FIGS. 8 and 9, the first light-emitting element 101 and the first photodetector 201 are respectively located on the upper and lower sides of the first light blocking element 3011, such that the first light blocking element 3011 separates the first light-emitting element 101 from the first photodetector 102. In one preferred embodiment, the first light blocking element 301 or 3011 guides the light emitted by the first light-emitting element 101 to illuminate one or more corresponding areas of the testing element, and the light illumination range on the testing element is related to the distance between the first light-emitting element 101 and the testing element 40, and the height of the first light blocking element 301 or 3011.

In a preferred embodiment, as shown in FIGS. 2 and 3 or as shown in FIGS. 8 and 9, the second light blocking element 302 or 3021 is located above the first photodetector 201, i.e. the second light blocking element 302 or 3021 is spatially located above the first photodetector 201, covering or partially covering the first photodetector 201, with a distance from the first photodetector 201.

In some embodiments, the testing element 40 can be a separate device that is introduced into the reading apparatus for the detection of the analyte, for example, a lateral flow test strip. The testing element 40 is detachably combined with the reading apparatus, when the testing element 40 is fixed together with the reading apparatus, the first light-emitting element 101, the first photodetector 201 and the testing element 40 form a detection space for detecting an analyte. In some embodiments, the testing element 40 is a lateral flow test strip having a sample absorption area 401, a reagent area 402, a testing area 403, a control area 405, and a water absorption area 406, or there is a reference area 404 between the testing area 403 and the control area 405; wherein, the testing area 403 is an area where the light signal is formed in the testing element (for example, a stacking area or a storage area of labeled substance of a particulate colored binding reagent), indicating the presence or absence of the analyte. The control area 405 is used to display whether the detection is carried out properly, regardless of the presence or absence of the analyte. The reference area 404 is the area that forms the background signal that can be used to calibrate the reading apparatus or provide a background signal that can be referenced for the test signal.

In one preferred embodiment, when the testing element 40 is fixed to the reading apparatus, the second light blocking element 302 or 3021 is located between the first photodetector 201 and the testing element 40, that is, the second light blocking element 302 or 3021 is spatially located between the first photodetector 201 and the testing element 40. The second light blocking element 302 or 3021 may be in contact with the testing element 40 or may have a certain gap with the testing element 40. In one preferred embodiment, when the testing element 40 is fixed to the reading apparatus, the second light blocking element 302 or 3021 is in contact with one or more corresponding areas of the testing element 40, to cover the one or more corresponding areas of the testing element 40, and separate one or more areas of the testing element 40, or separate one or more areas of the testing element 40 and separate the first photodetector 20, to block the light emitted by the first light-emitting element 101 from illuminating the areas of the testing element 40 that are covered by the second light blocking element 302 or 3021, and/or block the light from the areas of testing element 40 that are covered by the second light blocking element 302 or 3021 from entering the first photodetector 201, that is, guiding the light from the areas of the testing element 40 that reflect the accumulation of labeled substances from entering the first photodetector 201. In one preferred embodiment, when the testing element 40 is fixed to the reading apparatus, the second light blocking element 302 or 3021 is spaced apart from one or more corresponding areas of the testing element 40, and spatially covers one or more corresponding areas of the testing element 40, such that the light emitted by the first light-emitting element 101 cannot illuminate the covered areas of the testing element 40, or the light from the covered area of the testing element 40 cannot enter the first photodetector 201.

In one preferred embodiment, as shown in FIGS. 2 and 3, the second light blocking element 302 is disposed in an area between the testing area 403 and the control area 405 corresponding to the testing element 40, to separate the testing area 403 from the control area 405 of the testing element 40 and thereby block the light emitted from the first light-emitting element 101 from illuminating the area between the testing area 403 and the control area 405 of the testing element 40, and/or block the light from the area between the testing area 403 and the control area 405 of the testing element 40 from entering the first photodetector 201. In one preferred embodiment, the second light blocking element 302 is disposed in an area corresponding to the reference area 404 of the testing element 40, thereby blocking the light emitted by the first light-emitting element 101 from illuminating the reference area 404 of the testing element 40, and/or blocking the light from the reference area 404 of the testing element from entering the first photodetector 201. The light from the area between the testing area 403 and the control area 405 of the testing element, or the light from the testing element reference area 404, is independent of the presence or absence of the analyte, which blocks the light emitted from the first light-emitting element 101 from illuminating the area, or blocks the light from this area from entering the first photodetector 201, so as to effectively avoid the impact of invalid light on the detection result, and improve the detection sensitivity and accuracy.

In one preferred embodiment, as shown in FIGS. 8 and 9, the second light blocking element 3021 is disposed in an area corresponding to the testing area 403 or the control area 405 of the testing element 40, partially covering the testing area 403 or the control area 405.

In one preferred embodiment, a longitudinal extension of the first light blocking element 301 intersects with the testing element 40, and the second light blocking element 302 or 3021 is longitudinally parallel to the testing element 40, and the second light blocking element 302 or 3021 and the first light blocking element 301 are disposed in a mutually perpendicular manner, i.e. the longitudinal extension line of the first light blocking element 301 intersects the lateral extension line of the second light blocking element 302 or 3021 at an included angle of 90°.

In one preferred embodiment, as shown in FIGS. 1-4, the apparatus further comprises a third light blocking element 303, wherein the first photodetector 201 is located between the first light blocking element 301 and the third light blocking element 303. In one preferred embodiment, the second light blocking element 302 is located between the first light blocking element 301 and the third light blocking element 302 and covers the photodetector 201.

In one preferred embodiment, a second light-emitting element 102 is disposed outside the third light blocking element 303, and the first light blocking element 301 and the third light blocking element 303 respectively separate the first light-emitting element 101 and the second light-emitting element 102 from the first photodetector 201 to ensure that the light emitted by each light emitting element illuminates the corresponding area of the testing element only, without illuminating the photodetector.

In one preferred embodiment, the first light-emitting element 101 and/or the second light-emitting element 102 are linearly arranged with the first photodetector 201. Wherein, the first light-emitting element 101 or the second light-emitting element 102 corresponds to the location of the testing area 403 or the control area 405 of the testing element respectively, and the emitted light illuminates the testing area 403 or the control area 405 respectively.

In one preferred embodiment, the first light-emitting element 101 and the second light-emitting element 102 are linearly arranged with the first photodetector 201, and the first photodetector 201 is disposed in the middle of the above two light emitting elements, that is, the two light emitting elements share a photodetector. Wherein, the first light-emitting element 101 corresponds to the testing area 403 of the testing element 40, and the second light-emitting element 102 corresponds to the control area 405 of the testing element; wherein the first light blocking element 301 is located between the first light-emitting element 101 and the first photodetector 201, to block the light emitted by the first light-emitting element 101 from entering the first photodetector 201, and the third light blocking element 303 is located between the second light-emitting element 102 and the first photodetector 201, to block the light emitted by the second light-emitting element 102 from entering the first photodetector 201, and the second light blocking element 302 is located between the first light blocking element 301 and the third light blocking element 303 and covers the photodetector 201, and corresponds to the area between the testing area 403 and the control area 405 of the testing element 40, or corresponds to the reference area 404 of the testing element 40, to separate the testing area 403 from the control area 405 of the testing element 40. With such arrangement, the light emitted by the two light emitting elements illuminates the testing area 403 and the control area 405 of the testing element 40 respectively, without illuminating the area between the testing area 403 and the control area 405 of the testing element 40, or without illuminating the reference area 404. The first photodetector 201 also receives the light from the testing area 403 and the control area 405 sequentially, without receiving light from the area between the testing area 403 and the control area 405 or light from the reference area 404, thereby improving the detection sensitivity and accuracy.

In one preferred embodiment, the light blocking element has a gap that transmits light from the testing element 50. In one preferred embodiment, the gap 50 is disposed in an area where a testing area or a control area of the testing element is located.

In one preferred embodiment, as shown in FIGS. 1-4, when the testing element 40 is fixed to the reading apparatus, the second light blocking element 302 is in contact with the testing element 40, and the first light blocking element 301 is not in contact with the testing element 40, and a first gap 501 is provided between the first light blocking element 301 and the second light blocking element 302 for transmitting light from the testing element 40. Specifically, the height of the first light blocking element 301 is smaller than the vertical distance between the testing element 40 and the first light-emitting element 101, and the second light blocking element 302 is not in contact with the first light blocking element 301, with a space, thereby a first gap 501 is formed between the first light blocking element 301 and the second light blocking element 302 for transmitting light from the testing element. In one preferred embodiment, the gap is a slanted gap, that is, the first gap 501 is a slanted gap, specifically, the side of the first light blocking element 301 and/or the second light blocking element 302 adjacent to the first photodetector 201 is a slope, thereby forming a slanted first gap 501. The setting of this slope can further reduce the blocking of light by the first light blocking element 301 and/or the second light blocking element 302, to facilitate the light from the testing element 40 to enter the first photodetector 201 and ensure that the first photodetector 201 receives the maximum area of light from the corresponding area of the testing element to achieve better detection effect.

In one preferred embodiment, when the testing element 40 is fixed to the reading apparatus, the second light blocking element 302 is in contact with the testing element 40, and the third light blocking element 303 is not in contact with the testing element 40, and a second gap 502 is provided between the third light blocking element 303 and the second light blocking element 302 for transmitting light from the testing element 40. Specifically, the height of the third light blocking element 303 is smaller than the vertical distance between the testing element 40 and the second light-emitting element 102, and the second light blocking element 302 is not in contact with the third light blocking element 303 with a space, thereby a second gap 502 is formed between the second light blocking element 302 and the third light blocking element 303 for transmitting light from the testing element 40. In one preferred embodiment, the second gap 502 is a slanted gap, specifically, the side of the third light blocking element 303 and/or the second light blocking element 302 adjacent to the first photodetector 201 is a slope, thereby forming a slanted second gap 502. The setting of this slope can further reduce the blocking of light by the third light blocking element 303 and/or the second light blocking element 302, to facilitate the light from the testing element 40 to enter the first photodetector 201.

In other words, in the above embodiment, the second light blocking element 302 is spatially located between the first light blocking element 301 and the third light blocking element 303, and the width of the second light blocking element 302 is equal to or smaller than the horizontal distance between the first light blocking element 301 and the third light blocking element 303, and the height of the first light blocking element 301 and the third light blocking element 303 is less than the vertical distance between the testing element 40 and the light emitting element, thereby forming the first gap 501 and the second gap 502 described above.

In one preferred embodiment, the first, second, and third light blocking elements are of rectangular slab structures. When the side of the first light blocking element 301 and/or the second light blocking element 302 and/or the third light blocking element 303 adjacent to the photodetector is a slope, the width of the second light blocking element 302 is equal to or smaller than the horizontal distance between the first light blocking element 301 and the third light blocking element 303.

In one preferred embodiment, the reading apparatus further comprises a fourth light blocking element 304 and a fifth light blocking element 305, and the fourth light blocking element 304 and the fifth light blocking element 305 are respectively located above the first light-emitting element 101 and the second light-emitting element 102 to cover or partially cover the first light-emitting element 101 and the second light-emitting element 102. In one preferred embodiment, the fourth light blocking element 304 is spatially located outside the first light blocking element 301, and the fifth light blocking element 305 is spatially located outside the third light blocking element 303 for further defining the illumination range of the light emitted by the first light-emitting element 101 and the second light-emitting element 102 on the testing element 40. In one preferred embodiment, the fourth light blocking element 304 and the fifth light blocking element 305 are respectively located on both sides of the second light blocking element 302, and are longitudinally parallel with the testing element 40. When the testing element 40 is fixed to the reading apparatus, the fourth light blocking element 304 and the fifth light blocking element 305 are in contact with the testing element 40, covering the corresponding area of the testing element 40. In one preferred embodiment, when the testing element 40 is fixed to the reading apparatus, the fourth light blocking element 304 covers the area in front of the testing area of the testing element, to block the light emitted by the first light-emitting element 101 from illuminating the testing area in front of the testing area of the testing element. In one preferred embodiment, when the testing element 40 is fixed to the reading apparatus, the fifth light blocking element 305 covers the area behind the control area of the testing element, to block the light emitted by the second light-emitting element 102 from illuminating the area behind the control area of the testing element.

In one preferred embodiment, there are a third gap 503 and a fourth gap 504 between the light blocking element 304 and the first light blocking element 301, and between the fifth light blocking element 305 and the third light blocking element 303, respectively, for allowing the light emitted from the first light-emitting element 101 and the second light-emitting element 102 to illuminate the testing element 40. The fourth light blocking element 304 and the fifth light blocking element 305 guide the light emitted from the light emitting element to illuminate a specific area of the testing element only, preferably illuminate the testing area 403 and the control area 405 of the testing element only, or illuminate the area where the testing line and the control line of the testing element are located.

In one preferred embodiment, the first to fifth light blocking elements mutually cooperate to further define the light path and the light illumination area. Specifically, the light emitted from the first light-emitting element 101 only illuminates the testing area 403 of the testing element 40 through the third gap 503, and then the light from the testing area 403 of the testing element is received by the first photodetector 201 through the first gap 501. The light emitted from the second light-emitting element 102 only illuminates the control area 405 of the testing element 40 through the fourth gap 504, and then the light from the control area 405 of the testing element is received by the first photodetector 201 through the second gap 502. By the foregoing optical path optimization, the light emitted by the light emitting element illuminates only the testing area 403 and the control area 405 of the testing element, such that the valid light from the testing element that can reflect the detection result is received by the photodetector and other invalid light is prevented from entering the photodetector, thereby comprehensively enhancing the detection sensitivity and accuracy.

In another particular embodiment, referring to FIGS. 7-12, the light blocking element 30 further comprises a third light blocking element 3031, and a second photodetector 202 is disposed outside the third light blocking element 3031, that is, a third light blocking element 3031 is located between two photodetectors to separate the two photodetectors. In one preferred embodiment, the two photodetectors share a third light blocking element 3031, that is, two adjacent photodetectors are separated by a third light blocking element 3031 disposed therebetween. In one preferred embodiment, the two photodetectors are separated by two third light blocking elements 3031 that are independent of each other. In one preferred embodiment, the two third light blocking elements 3031 for separating two adjacent photodetectors are separated by a distance. In one preferred embodiment, the two third light blocking elements 3031 for separating the two adjacent photodetectors are longitudinally parallel. In one preferred embodiment, the area between the two third light blocking elements 3031 for separating the two adjacent photodetectors corresponds to the reference area 404 of the testing element.

In one preferred embodiment, the first light blocking element 3011 is connected to the third light blocking element 3031. In one preferred embodiment, the angle between the first light blocking element 3011 and the third light blocking element 3031 at the junction is 90°, that is, the first light blocking element 3011 and the third light blocking element 3031 present a vertical structure. In one preferred embodiment, the second light blocking element 3021 is located above the first light blocking element 3011 and the third light blocking element 3011, that is, the second light blocking element 3021 covers the first light blocking element 3011 and the third light blocking element 3031. In one preferred embodiment, the second light blocking element 3021 and the first light blocking element 3011 and the third light blocking element 3031 present a vertical structure. In one preferred embodiment, the longitudinal extension of the first light blocking element 3011 intersects with the testing element 40 and is perpendicular to the short axis of the testing element 40. The second light blocking element 3021 is in contact with the testing element 40, presenting a longitudinal parallel structure. The longitudinal extension of the third light blocking element 3031 intersects with the testing element 40 and is perpendicular to the long axis of the testing element 40. In one preferred embodiment, a light blocking element composed of a first light blocking element 3011, a second light blocking element 3021, and a third light blocking element 3031 separates at least one photodetector in a separate space.

In one preferred embodiment, the apparatus further comprises a second light-emitting element 102, and the first light-emitting element 101 and the second light-emitting element 102 are respectively disposed at a position corresponding to the testing area 403 or the control area 405 of the testing element. In one preferred embodiment, the first light-emitting element 101 and the second light-emitting element 102 are respectively disposed opposite the first photodetector 201 and the second photodetector 202, and a light blocking element 30 is disposed between the light emitting element and the photodetector. In one preferred embodiment, there is no light blocking element 30 between the first light-emitting element 101 and the second light-emitting element 102. In one preferred embodiment, there is a third photodetector 203 between the two light emitting elements for initial calibration or dimming of the apparatus.

Figure 7:
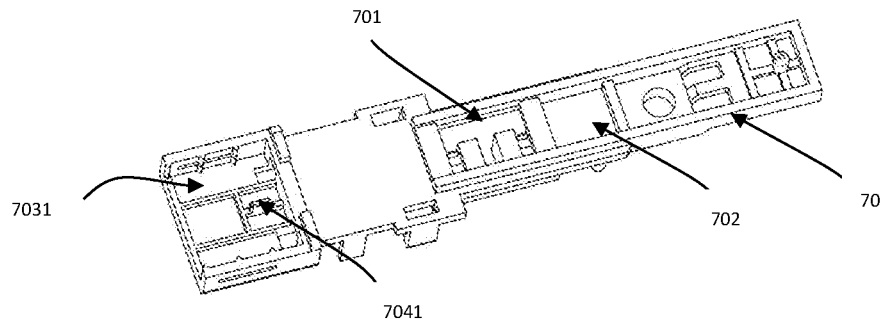
FIG. 7 is a schematic perspective view of a reading apparatus according to another particular embodiment of the present invention.

In one preferred embodiment, as shown in FIG. 7-9, there is a gap 50 on the light blocking element 30 for transmitting light from the testing element, and the setting of the gap 50 enables the light from a corresponding area of the testing element to enter the photodetector through the gap 50, and the light from another area of the testing element cannot enter the photodetector. The gap 50 is used to guide the light of the corresponding area of the testing element to enter the photodetector on one hand, and guide the path of the light emitted by the light emitting element, such that the light emitted from the light emitting element can illuminate desirable areas of the testing element as much as possible. In one preferred embodiment, the gap 50 is disposed at a position corresponding to the testing area or the control area of the testing element, to guide the light from the testing area or the control area of the testing element to be received by the photodetector. In one preferred embodiment, the gap 50 includes a first gap 5011 and/or a second gap 5012.

In one preferred embodiment, there is a first gap 5011 on the first light blocking element 3011. Specifically, the first light blocking element 3011 has a recess at a position close to the testing element 40. When the testing element 40 is fixed to the electronic reading apparatus, a first gap 5011 is formed at the recess between the first light blocking element 3011 and the testing element 40. The presence of the first gap 5011 reduces the blocking of the light of the light emitting element by the first light blocking element 3011 and the light from the testing element, such that the light from the corresponding area of the testing element can enter the photodetector through the first gap 5011 on one hand, and the light from light emitting element illuminates the corresponding area of the testing element in a larger scope on the other hand. In one preferred embodiment, the first gap 5011 is a slanted gap. Specifically, the recess on the first light blocking element 3011 is a slope on a side adjacent to the photodetector and/or the light emitting element, thereby forming a slanted first gap 5011. The setting of the slope can further reduce the blocking of the light of testing element and/or the light emitted from the light emitting element by the first light blocking element 3011, which, on one hand, facilitates the light from the corresponding area of the testing element 40 to enter the photodetector to ensure that the photodetector receives the largest area of light from the corresponding area of the testing element; and on the other hand, allows the light emitted from the light emitting element to illuminate the corresponding area of the testing element as much as possible to achieve better detection effect. In one preferred embodiment, the first gap 5011 is disposed corresponding to the testing area 403 or the control area 405 of the testing element. In one preferred embodiment, the first gap 5011 is disposed corresponding to the position where the testing line or control line of the testing element is located. In one preferred embodiment, the width of the first gap 5011, i.e. the length of the groove located on the first light blocking element 3011 is equal to or smaller than the width of the testing area 403 or the control area 405 of the testing element.

In one preferred embodiment, there is a second gap 5012 on the second light blocking element 3021. When the testing element 40 is fixed on the reading apparatus, the area of the testing element that is in contact with the second gap 5012 is not covered. The presence of the second gap 5012 reduces the blocking of the light emitted from the light emitting element by the second light blocking element 3021 such that, on one hand, the light from the area of the testing element that is in contact with the second gap 5012 and is not covered by the second light blocking element 3021 can enter the photodetector through the second gap 5012, and on the other hand, the light from the light emitting element can illuminate the corresponding area of the testing element in a larger scope, that is, the light from the light emitting element can illuminate the area of the testing element that is in contact with the second gap 5012 and is not covered by the second light blocking element 3021. In one preferred embodiment, the second gap 5012 is disposed corresponding to the testing area 403 or the control area 405 of the testing element, that is, when the testing element is fixed on the reading apparatus, part of the testing area or the control area of the testing element is not covered by the second light blocking element 3021. In one preferred embodiment, the second gap 5012 is disposed in a position where the testing line or the control line of the testing element is located. In one preferred embodiment, the width of the second gap 5012 is equal to or smaller than the width of the testing area 403 or the control area 405 of the testing element. The second light blocking element 3021 can be considered as a sheet structure disposed between the testing element and the photodetector, and the sheet structure has a hollowed area at a position corresponding to the testing area or the control area of the testing element, thereby forming a second gap 5012. The second light blocking element 3021 may also be considered to be divided into a fourth light blocking element 3041 and a fifth light blocking element 3051 which are separated from each other at the second gap 5012, or it can be considered that the second light blocking element 3021 is composed of a fourth light blocking element 3041 and a fifth light blocking element 3051 which are separated from each other, and a second gap 5012 is formed in an area where the fourth light blocking element 3041 and the fifth light blocking element 3051 are separated from each other. The distance between the fourth light blocking element 3041 and the fifth light blocking element 3051 is equal to the width of the second gap 5012.

In one preferred embodiment, the first gap 5011 is in communication with the second gap 5012. Specifically, the first gap 5011 and the second gap 5012 are disposed at the same position relative to the testing area 403 or the control area 405, and there is no connection piece between the first gap 5011 and the second gap 5012, that is, the first gap 5011 and the second gap 5012 are combined together such that the light blocking element 30 has a L-shaped gap 50. In one preferred embodiment, the width of the first gap 5011 is equal to the width of the second gap 5012. In one preferred embodiment, the width of the first gap 5011 is not equal to the width of the second gap 5012. In one preferred embodiment, there is a connection piece between the first gap 5011 and the second gap 5012, such that the first gap 5011 is not in communication with the second gap 5012. The shape and size of the connection piece is not limited, which may be a strip structure or a sheet structure, as long as the first gap 5011 and the second gap 5012 are not completely covered. In one preferred embodiment, there is offset between the position of the first gap 5011 and that of the second gap 5012. As there is a certain range of the width of the testing area 403 or the control area 405, the offset between the first gap 5011 and the second gap 5012 can guarantee that the gap 50 is located at a position where the testing area 403 or the control area 405 is located. In one preferred embodiment, when there is a second gap 5012 on the second light blocking element 3021, there may be no first gap 5011 on the first light blocking element 3011.

In one preferred embodiment, there is no gap on the third light blocking element 3031, such that the light entering the separated space cannot enter another photodetector.

Reading Apparatus

The reading apparatus refers to an apparatus for reading the test results on the testing element. The reading apparatus referred to in the present invention may comprise the testing element 40 or may not comprise the testing element 40. As described above, the testing element 40 can be a separate device that is introduced into the reading apparatus for detection of analyte or an integral part of the reading apparatus. If the testing element 40 is an integral part of the reading apparatus, the reading apparatus may comprise a testing element 40 for microfluidic detection or lateral chromatographic detection. The reading apparatus may comprise a space for accommodating the testing element 40 but not necessarily comprise a testing element 40. The testing element 40 may be combined with the reading apparatus at any appropriate time thereafter. When the reading apparatus comprises the testing element 40, it can also be regarded as a detection apparatus for detecting the presence or absence of analyte in the samples, that is, the reading apparatus of the present invention is substantially a detection apparatus for detecting the analyte in the samples. Any analyte can be detected using the apparatus of the present invention and an appropriate testing element. Preferably, the apparatus in the present invention is used for detection of early pregnancy.

In one particular embodiment, referring to FIGS. 1-5, the reading apparatus of the present invention comprises a first light-emitting element 101, emitting light and illuminating one or more corresponding areas of the testing element 40; a first photodetector 201, receiving light from one or more corresponding areas of the testing element 40; a light blocking element, for guiding a path of light emitted from a light emitting element and/or from a testing element, wherein the light blocking element comprises a first light blocking element 301 and a second light blocking element 302, the first light blocking element 301 is located between the first light-emitting element 101 and the first photodetector 201, to block the light from the first light-emitting element 101 from entering the first photodetector 201, and the second light blocking element 302 is located above the first photodetector 201, to guide the light from the testing element 40 to enter the photodetector 201.

In one preferred embodiment, the reading apparatus further comprises a second light-emitting element 102 and a third light blocking element 303, wherein the first light-emitting element 101 is located outside the first light blocking element 301, and the second light-emitting element 102 is located outside the third light blocking element 303. The first photodetector 201 is located between the first light blocking element 301 and the third light blocking element 303, and the first light-emitting element 101 and the second light-emitting element 102 are linearly arranged with the first photodetector 201. The first light blocking element 301 blocks the light from the first light-emitting element 101 from entering the first photodetector 201, and the third light blocking element 303 blocks the light from the second light-emitting element 102 from entering the first photodetector 201, the second light blocking element 302 is located above the first photodetector 201, and located between the first light blocking element 301 and the third light blocking element 302 to guide the light from the corresponding area of the testing element 40 to be received by the photodetector 201.

In one preferred embodiment, the reading apparatus further comprises a fourth light blocking element 304 and a fifth light blocking element 305, the fourth light blocking element 304 and the fifth light blocking element 305 are respectively located above the first light-emitting element 101 and the second light-emitting element 102, and correspond to the area in front of the testing area of the testing element and the area behind the control area of the testing element respectively, to block the light emitted by the first light-emitting element 101 from illuminating the area in front of the testing area of the testing element and block the light emitted by the second light-emitting element 102 from illuminating the area behind the control area of the testing element.

In one preferred embodiment, the reading apparatus further comprises a base board 60 and a base frame 70, wherein the light emitting element 101/102 and the photodetector 201 are located on the base board 60, the base board 60 is a PCB board; and the base frame 70 has a detection window 701. The light blocking element is located in the detection window 701 of the base frame 70. When the base board 60 is combined with the base frame 70 and the testing element 40 is fixed on the base frame 70, the detection window 701 encloses the first light-emitting element 101, the second light-emitting element 102, the first photodetector 201, and one or more areas of the testing element 40 in a confined space (FIG. 5).

In one preferred embodiment, the reading apparatus further comprises a housing for supporting the components of the reading apparatus and/or protecting them from the influence of external environment. The housing consists of an upper casing 80, a lower casing 90 and cover body 100 (FIG. 5).

In another particular embodiment, referring to FIGS. 7-13, the reading apparatus of the present invention comprises: a first light-emitting element 101 and a second light-emitting element 102, emitting light and illuminating one or more corresponding areas of the testing element 40; a first photodetector 201 and a second photodetector 202, receiving light from one or more corresponding areas of the testing element 40; and a light blocking element, for guiding a path of light emitted from a light emitting element and/or from a testing element, and separating the first photodetector 201 and the second photodetector 202 in separate spaces.

In one preferred embodiment, the first light-emitting element 101 and the first photodetector 201 are disposed at positions corresponding to the testing area 403 of the testing element, and the second light-emitting element 102 and the second photodetector 202 are disposed at positions corresponding to the control area 405 of the testing element. Wherein, the light blocking element comprising the first light blocking element 3011, the second light blocking element 3021 and the third light blocking element 3031 separates the first photodetector 201 in a separate space, and the light blocking element comprising the sixth light blocking element 3061, the seventh light blocking element 3071 and the eighth light blocking element 3081 separates the second photodetector 202 in a separate space. In one preferred embodiment, there is a gap 50 on the light blocking element that separates the first photodetector 201, and the gap 50 corresponds to the testing area 403 of the testing element, the gap 50 comprises a first gap 5011 on the first light blocking element 3011 and a second gap 5012 on the second light blocking element 3021, and the first gap 5011 is in communication with the second gap 5012. The second light blocking element 3021 is divided into a fourth light blocking element 3041 and a fifth light blocking element 3051 which are separated from each other at the second gap 5012, and thus it can be regarded that the light blocking element 30 comprising a first light blocking element 3011, a third light blocking element 3031, a fourth light blocking element 3041, and a fifth light blocking element 3051 encloses the first photodetector 201 in a separate space. In one preferred embodiment, there is a gap 50 on the light blocking element 30 separating the second photodetector 202. The gap 50 corresponds to the control area 405 of the testing element. The gap 50 comprises a first gap 5011 on the sixth light blocking element 3061 and a second gap 5012 on the seventh light blocking element 3071. The first gap 5011 is in communication with the second gap 5012. The seventh light blocking element 3071 is divided into a ninth light blocking element 3091 and a tenth light blocking element 3101 which are separated from each other at the second gap 5012, and thus it can be regarded that the light blocking element 30 comprising a sixth light blocking element 3061, an eighth light blocking element 3081, a ninth light blocking element 3091 and a tenth light blocking 3101 encloses the second photodetector 202 in a separate space (FIG. 9).

In one particular embodiment, as shown in FIG. 9, the light emitted by the first light-emitting element 101 can illuminate the testing area 403 of the testing element and the areas 407 and 408 near the testing area. Due to the presence of the fourth light blocking element 3041 and the fifth light blocking element 3051, the light like reflected light from the areas in front of and behind the testing area is blocked by the fourth light blocking element 3041 and the fifth light blocking element 3051 and unable to enter the first photodetector 201; since there is a second gap 5012 between the fourth light blocking element 3041 and the fifth light blocking element 3051, the second gap 5012 is disposed at a position corresponding to the testing area 403 of the testing element. Due to the presence of the second gap 5012, the testing area 403 above the first photodetector 201 is not covered by the light blocking element, such that the light emitted by the light emitting element can illuminate the testing area 403 of the testing element and the light from the testing area 403 of the testing element can be received by the first photodetector 201. In one particular embodiment, the light emitted by the second light-emitting element 102 can illuminate the control area 405 of the testing element and the areas 409 and 410 near the control area. Due to the presence of the ninth light blocking element 3091 and the tenth light blocking element 3101, the light from the areas in front of and behind the control area is blocked by the ninth light blocking element 3091 and the tenth light blocking element 3101 and unable to enter the second photodetector 202; since there is a second gap 5012 between the ninth light blocking element 3091 and the tenth light blocking element 3101, the second gap 5012 is disposed at a position corresponding to the control area 405 of the testing element. Due to the presence of the second gap 5012, the control area 405 above the second photodetector 202 is not covered by the light blocking element, such that the light emitted by the light emitting element can illuminate the control area 405 of the testing element and the light from the control area 405 of the testing element can be received by the second photodetector 202.

In one preferred embodiment, the light blocking elements constituting the light blocking element 30 mutually cooperate to further define a light path and a light illumination area. Specifically, the light emitted by the first light-emitting element 101 illuminates the testing area 403 of the testing element 40, and further the light from the testing area 403 of the testing element is received by the first photodetector 201 through the gap 50, and the light emitted by the second light-emitting element 102 illuminates the control area 405 of the testing element 40, and further the light from the control area 405 of the testing element is received by the second photodetector 202 through the gap 50. Through the optimization of optical path, the photodetector only receives the light from the testing area 403 and the control area 405 of the testing element, such that the valid light from the testing element that reflects the detection result is received by the photodetector and other invalid light is prevented from entering the photodetector, thereby comprehensively improving the detection sensitivity and accuracy. Moreover, with the setting of the gap 50 on the light blocking element, the light emitted from the first light-emitting element 101 and the second light-emitting element 102 illuminates the testing area 403 and the control area 405 of the testing element as much as possible respectively, and after reflection by the testing element, the light is received by the first photodetector 201 and second photodetector 202, which not only reduces the blocking of the light emitting element by the light blocking element, but also defines the optical path from the target area of the testing element.

It should be understood that, in the present invention, when referring to "the apparatus comprises a first light-emitting element or a first photodetector", it does not mean that the apparatus necessarily comprises a second light-emitting element or a second photodetector, and the apparatus may comprise only one light emitting element or only one photodetector, or may further comprise a second light-emitting element or a second photodetector.

It should be understood that, the terms used herein such as "first light blocking element", "second light blocking element", "third light blocking element", "first light blocking element", "second light blocking element", "first light-emitting element", "second light-emitting element", "first photodetector", "second photodetector", "first space", "second space", "first gap", "second gap", are used merely to facilitate the description of the electronic reading apparatus of the present invention, rather than constitute any limitation to the present invention.

Detachable Combination

A detachable combination means that the connection relationship of two parts is in several different states or locations, for example, when two physical parts are separated initially, they can connect or combine together at an appropriate first condition; and at an appropriate second condition, the two parts can be separated, and the separation is a separation of physical space, without contact. Or, the two parts are combined together initially, and when appropriate, the two parts can be separated physically, or two objects are separated initially, and when required, they combine together to complete some functions, and then separate, or combine again for some purposes subsequently. In a word, the combination or separation of two parts is easy, and such combination or separation can be repeated for many times, of course, it can be one-time combination or separation. In addition, the combination may be a detachable combination between two parts, or a mutually detachable combination between three or more parts.

It should be noted that when an element is referred to as being "fixed" to another element, it may be directly on the other element or connected through a connecting element. When one element is considered to be "connected" to another element, it can be directly connected to another element or through a connecting element. The term "and/or" used herein includes any and all combinations of one or more of the associated listed items.

Referring to FIG. 4, FIG. 5, FIG. 7 and FIG. 13, in some preferred particular embodiments, the light blocking element is located in the detection window 701 of the base frame 70, the light emitting element and the photodetector are disposed on the base board 60, and the base board 60 and the base frame 70 are detachably connected, combined or united. In one preferred embodiment, the testing element 40 is a separate device introduced to a reading apparatus, and the testing element 40 is detachably connected, combined or united with the reading apparatus. The base frame 70 is provided with a slot 702 for accommodating the testing element 40, and the testing element 40 is combined with the base frame when appropriate. When the base board 60 is combined with the base frame 70 and the testing element 40 is fixed on the base frame 70, the detection window 701 encloses the light emitting element, the photodetector, and one or more areas of the testing element 40 in a closed space for the reading or detection.

Detection Method

The present invention further provides a method for reading an assay result on a testing element, providing a reading apparatus as shown in FIGS. 1-5, wherein the apparatus comprising: a first light-emitting element 101, emitting light and illuminating one or more corresponding areas of the testing element; a first photodetector 201, receiving light from one or more corresponding areas of the testing element 40; a light blocking element, for guiding a path of light emitted from a light emitting element and/or from a testing element, such that the light from the testing element 40 is received by or substantially received by the first photodetector 201.

In some particular embodiments, the light blocking element includes a first light blocking element 301 and a second light blocking element 302, wherein the first light blocking element 301 is located between the first light-emitting element 101 and the first photodetector 201, such that the light emitted from the first light-emitting element 101 illuminates the testing element 40 without illuminating the first photodetector 201.

In some particular embodiments, the second light blocking element 302 is located above the first photodetector 201, such that the second light blocking element 302 guides the light from the testing element 40 to illuminate the first photodetector 201.

In some particular embodiments, the second light blocking element 302 is disposed between the first photodetector 201 and the testing element 40, to separate one or more corresponding areas of the testing element 40, or separate one or more corresponding areas of the testing element 40 from the first photodetector 201, such that the light from the corresponding area of the testing element 40 can be received by the first photodetector 201, and the light from another corresponding area of the testing element 40 cannot be received by the first photodetector 201.

In some particular embodiments, the second light blocking element 302 is disposed in an area between the testing area 403 and the control area 405 of the testing element 40, such that the light from the testing area 403 and/or the control area 405 of the testing element can be received by the first photodetector 201, and the light from the area between the testing area and the control area of the testing element cannot be received by the first photodetector 201.

In some particular embodiments, the second light blocking element 302 is disposed in the reference area 404 of the testing element 40, to separate the testing area 403 from the control area 405 of the testing element, such that the light from the testing area 403 and/or the control area 405 of the testing element can be received by the first photodetector 201, and the light from the reference area of the testing element cannot be received by the first photodetector 201.

In some particular embodiments, the extension of the first light blocking element 301 intersects the testing element 40, and the second light blocking element 302 is longitudinally parallel to the testing element 40.

In some particular embodiments, the second light blocking element 302 and the first light blocking element 301 are disposed in a mutually perpendicular form.

In some particular embodiments, the apparatus further comprises a third light blocking element 303, wherein the first photodetector 201 is located between the first light blocking element 301 and the third light blocking element 303

In some particular embodiments, the apparatus further comprises a third light blocking element 303, wherein the first photodetector 201 is located between the first light blocking element 301 and the third light blocking element 303.

In some particular embodiments, the second light blocking element 302 is located between the first light blocking element 301 and the third light blocking element 303, and the second light blocking element 302 covers the first photodetector 201.

In some particular embodiments, a second light-emitting element 102 is disposed outside the third light blocking element 303.

In some embodiments, the first light-emitting element 101 and the photodetector 201 are linearly arranged, or the first light-emitting element 101 and/or the second light-emitting element 102 are linearly arranged with the photodetector 201.

In some particular embodiments, the first light blocking element 301 and the second light blocking element 302 have a gap that transmits light from the testing element 40.

In some embodiments, the gap is a slanted gap, such that the light from the testing element 40 is received by the first photodetector 201 through the slanted gap.

In some particular embodiments, the first light-emitting element 101 corresponds to the testing area 403 of the testing element, and the second light-emitting element 102 corresponds to the control area 405 of the testing element, the first light-emitting element 101 and the second light-emitting element 102 sequentially emit light, and the light illuminates the testing area 403 and the control area 405 of the testing element, and is received by the first photodetector 201 after reflection, to form an electrical signal for determining the detection result.

In some particular embodiments, the reading apparatus further comprises a fourth light blocking element 304 and a fifth light blocking element 305, and the fourth light blocking element 304 and the fifth light blocking element 305 are respectively located above the first light-emitting element 101 and the second light-emitting element 102 to cover or partially cover the first light-emitting element 101 and the second light-emitting element 102.

In some particular embodiments, the fourth light blocking element 304 and the fifth light blocking 305 are respectively located on both sides of the second light blocking element 302 and are not in contact with the second light blocking element 302, and are longitudinally parallel with the testing element 40. When the testing element 40 is fixed on the reading apparatus, the fourth light blocking element 304 and the fifth light blocking element 305 are brought into contact with the testing element 40 to cover the corresponding area of the testing element 40.

In some particular embodiments, the fourth light blocking element 304 covers the area in front of the testing area of the testing element, to block the light emitted by the first light-emitting element 101 from illuminating the area in front of the testing area of the testing element.

In some particular embodiments, the fifth light blocking element 305 covers the area behind the control area of the testing element, to block the light emitted by the second light-emitting element 102 from illuminating the area behind the control area of the testing element.

In some particular embodiments, there is a gap between the fourth light blocking element 304 and the first light blocking element 301, between the fifth light blocking element 305 and the third light blocking element 303 respectively to allow the light emitted from the first light-emitting element 101 and the second light-emitting element 102 to illuminate the testing element 40.

The steps of applying the reading apparatus to read the test result on the testing element or detect the analyte comprise: (1) applying a liquid sample to the testing element 40, to allow liquid to flow on the testing element 40 and accumulate the labeled substance in the testing area 403 of the testing element; (2) allowing the first light-emitting element 101 and second light-emitting element 102 to sequentially emit light by program control, wherein the light from the first light-emitting element 101 illuminates the testing area 403 of the testing element through the third gap 503, after reflection, the light is received by the first photodetector 201 through the first gap 501; the light from the second light-emitting element 102 illuminates the control area 405 of the testing element through the fourth gap, and after reflection, the light is received by the first photodetector 201 through the second gap 502; (3) forming electrical signal that can be detected by the first photodetector 201 for determination and analysis of test results.

The present invention provides another method for reading an assay result on a testing element, providing a reading apparatus as shown in FIGS. 7-13, wherein the apparatus comprising: a first light-emitting element 101, emitting light and illuminating one or more corresponding areas of the testing element; a first photodetector 201, receiving light from one or more corresponding areas of the testing element; and a light blocking element 30, for guiding a path of light emitted from a light emitting element and/or from a testing element.

In one preferred embodiment, the light blocking element 30 separates the first photodetector 201 in a separate space, such that the light from a special area of the testing element enters the first photodetector 201.

In one preferred embodiment, the light blocking element includes a first light blocking element 3011 and a second light blocking element 3011, wherein the first light blocking element 3011 is located between the first light-emitting element 101 and the first photodetector 201, to guide the light emitted from the light emitting element to illuminate one or more areas of the testing element.

In one preferred embodiment, the second light blocking element 3021 is located above the first photodetector 201, such that the light from the testing element or light from a specific area of the test element is received by the first photodetector 201.

In one preferred embodiment, the light blocking element 30 has a gap 50 that transmits light from the testing element, such that the light from a specific area of the testing element enters the first photodetector 201 through the gap 50.

In one preferred embodiment, the gap 50 is disposed at a position corresponding to the testing area 403 or the control area 405 of the testing element, such that the light from testing area 403 or the control area 405 of the testing element enters the first photodetector 201 through the gap 50.

In one preferred embodiment, the gap 50 includes a first gap 5011 and/or a second gap 5012.

In one preferred embodiment, the first light blocking element 3011 has a first gap 5011.

In one preferred embodiment, the first gap 5011 is a slanted gap.

In one preferred embodiment, the second light blocking element 3021 has a second gap 5012.

In one preferred embodiment, the second gap 5012 is in communication with the first gap 5011.

In one preferred embodiment, the light blocking element 30 further includes a third light blocking element 3031, and a second photodetector 202 is disposed outside the third light blocking element 3031.

In one preferred embodiment, the apparatus further comprises a second light-emitting element 102, the first light-emitting element 101 and the second light-emitting element 102 are respectively disposed at positions corresponding to the testing area 403 or the control area 405 of the testing element, such that the light from the light emitting element illuminates the testing area 403 or the control area 405 of the testing element.

In one preferred embodiment, there is no light blocking element 30 between the first light-emitting element 101 and the second light-emitting element 102.

In one preferred embodiment, a third photodetector 203 is provided between the first light-emitting element 101 and the second light-emitting element 102.

In one preferred embodiment, the at least two light emitting elements and/or the third photodetector 203 are linearly arranged.

In one preferred embodiment, the first light-emitting element 101 and the second light-emitting element 102 sequentially emit light, and the light illuminates the testing area 403 and the control area 405 of the testing element, and enters the first photodetector 201 and the second photodetector 202 after reflection, to form an electrical signal for determining the detection result, which is used for determination of test results.

The steps of applying the second kind of reading apparatus of the present invention to read the test result on the testing element or detect the analyte comprise: (1) allowing the first light-emitting element 101 and second light-emitting element 102 to emit light by program control, and the third photodetector 203 to perform initial calibration or dimming of the apparatus; (2) applying a liquid sample to the testing element 40, to allow liquid to flow on the testing element 40 and accumulate the labeled substance in the testing area 403 of the testing element; (3) allowing the first light-emitting element 101 and second light-emitting element 102 to sequentially emit light by program control, wherein the light from the first light-emitting element 101 illuminates the testing area 403 of the testing element, after reflection, the light is received by the first photodetector 201 through the gap 50; the light from the second light-emitting element 102 illuminates the control area 405 of the testing element, and after reflection, the light is received by the second photodetector 202 through the gap 50; (3) forming electrical signal that can be detected by the first photodetector 201 and the second photodetector 202 for determination and analysis of test results.

DETAILED DESCRIPTION OF THE EMBODIMENT

The technical solutions in the embodiments of the present invention are clearly and completely described in the following with reference to the accompanying drawings, which are only a part of the embodiments of the present invention rather than all embodiments. All other technical solutions obtained by those skilled in the art based on the embodiments of the present invention without creative work are within the scope of protection of the present invention.

It should be understood that, the terms "above", "before", "after" and "outside" that indicate the orientation or positional relationship are based on the orientation or positional relationship shown in the drawings, which are intended for description of the present invention and simplified description, and are not intended to indicate or imply that the apparatus or element must have a particular a particular orientation and be operated in a particular orientation, therefore, it cannot be understood to limit the present invention.

Example 1

In the present embodiment, the present invention provides a reading apparatus for reading an assay result on a testing element, wherein the apparatus comprising: a first light-emitting element 101 and a second light-emitting element 102, emitting light and illuminating one or more corresponding areas of the testing element 40; a first photodetector 201, receiving light from one or more corresponding areas of the testing element 40; and a light blocking element, for guiding a path of light emitted from a light emitting element and/or from a testing element, such that light from the testing element is received by or substantially received by the photodetector (FIG. 1).

Specifically, the light emitting element is used to emit light, such as various light sources, in one particular embodiment, the light emitting element is a light emitting diode, for example, a LED light. The first photodetector 201 is used to detect the light illuminating thereon and convert it into a detectable electrical signal. In one particular embodiment, the first photodetector 201 is a photodiode (PD detector).

The light blocking element includes a first, a second, and a third light blocking elements, wherein the first photodetector 201 is located between the first light blocking element 301 and the third light blocking element 303, wherein the second light blocking element 302 is located above the first photodetector 201, and located between the first light blocking element 301 and the third light blocking element 303.

In one particular embodiment, the first light-emitting element 101 is located outside the first light blocking element 301, the second light-emitting element 102 is located outside the third light blocking element 303, and the first photodetector 201 is located between the first light blocking element 301 and the third light blocking element 303, such that the first light-emitting element 101 and the second light-emitting element 102 are separated from the photodetector 201, respectively.

In one particular embodiment, the second light blocking element 302 is longitudinally parallel to the testing element 40, and the longitudinal extension of the first light blocking element 301 and the third light blocking element 303 intersects the testing element 40.

In one particular embodiment, when the testing element 40 is fixed on the reading apparatus, the first light blocking element 301 and the third light blocking element 303 are not in contact with the testing element 40, and the second light blocking element 302 is in contact with the testing element 40 and is located between the first photodetector 201 and the testing elements 40, to separate one or more areas of the testing element 40, or separate one or more areas of the testing element 40 from the first photodetector 201.

In one particular embodiment, the second light blocking element 302 is disposed corresponding to an area between the testing area 403 and the control area 405 of the testing element, or disposed corresponding to the reference area 404 of the testing element. When the testing element 40 is fixed on the reading apparatus, the second light blocking element 302 is in contact with the area between the testing area 403 and the control area 405 of the testing element, or the second light blocking element 302 is in contact with the reference area 404 of the testing element, thereby separating the testing area 403 of the testing element from the control area 405, or separating the area between the testing area 403 and the control area 405 of the testing element from the first photodetector 20, or separating the reference area 404 of the testing element from the first photodetector 201, to prevent the light emitted from the light emitting element from illuminating the area, and/or prevent the light from the area from entering the first photodetector 201 which would produce interference on the detection results.

In one particular embodiment, a first gap 501 and a second gap 502 are formed between the first light blocking element 301 and the second light blocking element 302, and between the third light blocking element 303 and the second light blocking element 302 for transmitting the light from the testing element 40. Preferably, the gap is a slanted gap. Specifically, the heights of the first light blocking element 301 and the third light blocking element 303 are smaller than the vertical distance between the testing element 40 and the light emitting element, and the second light blocking element 302 is not in contact with the first light blocking element 301 and the third light blocking element 303, thus, a first gap 501 and a second gap 502 are formed between the first light blocking element 301 and the second light blocking element 302, and between the third light blocking element 303 and the second light blocking element 302 for transmitting the light from the testing element 40. Further, the side of the first light blocking element 301 and/or the second light blocking element 302 and/or the third light blocking element 303 adjacent to the photodetector 201 is a slope, thereby forming a slanted gap for light transmission.

In one preferred embodiment, the reading apparatus further comprises a fourth light blocking element 304 and a fifth light blocking element 305, and the fourth light blocking element 304 and the fifth light blocking element 305 are respectively located above the first light-emitting element 101 and the second light-emitting element 102 to cover or partially cover the first light-emitting element 101 and the second light-emitting element 102. In one preferred embodiment, the fourth light blocking element 304 is spatially located outside the first light blocking element 301, and the fifth light blocking element 305 is spatially located outside the third light blocking element 303 for further defining the illumination range of the light emitted by the first light-emitting element 101 and the second light-emitting element 102 on the testing element 40. In one preferred embodiment, the fourth light blocking element 304 and the fifth light blocking element 305 are respectively located on both sides of the second light blocking element 302 without contacting with the second light blocking element 302, and are longitudinally parallel with the testing element 40. When the testing element 40 is fixed to the reading apparatus, the second light blocking element 302, the fourth light blocking element 304 and the fifth light blocking element 305 are in contact with the testing element, covering the corresponding area of the testing element 40. In one preferred embodiment, when the testing element 40 is fixed to the reading apparatus, the fourth light blocking element 304 covers the area in front of the testing area of the testing element, to block the light emitted by the first light-emitting element 101 from illuminating the area in front of the testing area of the testing element. In one preferred embodiment, when the testing element 40 is fixed to the reading apparatus, the fifth light blocking element 305 covers the area behind the control area of the testing element, to block the light emitted by the second light-emitting element 102 from illuminating the area behind the control area of the testing element.

In one preferred embodiment, the first to fifth light blocking elements mutually cooperate to further define the light path and the light illumination area. Specifically, the light emitted from the first light-emitting element 101 only illuminates the testing area 403 of the testing element 40 through the third gap 503, and then the light from the testing area 403 of the testing element is received by the first photodetector 201 through the first gap 501. The light emitted from the second light-emitting element 102 only illuminates the control area 405 of the testing element 40 through the fourth gap 504, and then the light from the control area 405 of the testing element is received by the first photodetector 201 through the second gap 502. By the foregoing optical path optimization, the optical path and the light illumination area are further effectively defined to enhance the sensitivity and accuracy of the detection result.

In one embodiment, the apparatus comprises a lateral flow testing element 40. As described above, the testing element 40 can be a separate device that is introduced into the reading apparatus for analyte detection, or the testing element 40 is an integral part of the reading apparatus. If the testing element is an integral part of the reading apparatus, the reading apparatus may comprise a testing element 40 for microfluidic detection or lateral chromatographic detection.

In one particular embodiment, the reading apparatus may comprise a slot or other opening for accommodating the testing element 40 to insert to the reading apparatus. The shape and size of the slot or opening should allow successful insertion of a testing element 40 in an appropriate direction.

In one particular embodiment, the first light-emitting element 101 and the second light-emitting element 102 are linearly arranged with the first photodetector 201, and the first photodetector 201 is located between the first light-emitting element 101 and the second light-emitting element 102, wherein, the first light-emitting element 101 corresponds to the testing area 403 of the testing element, the second light-emitting element 102 corresponds to the control area 405 of the testing element, and the photodetector 201 corresponds to the area between the testing area 403 and the control area 405 of the testing element, or the reference area 404.

In one preferred embodiment, the reading apparatus comprises a processor for receiving electrical signals and performing analysis and result determination. The processor controls the two light emitting elements to sequentially emit light and illuminate the testing area 403 and control area 405 of the testing element 40. The photodetector receives the light from the testing area 403 and the control area 405 and converts it into an electrical signal, and the processor receives the electrical signal of the photodetector for reading and analysis.

In one preferred embodiment, the reading apparatus further comprises a display 130 and a power supply element 140. The processor displays the processing result on the display 130 to facilitate observation of the detection results. The power supply element 140 provides power for the entire photodetection system, for example, a power supply element such as a button battery may be used (FIG. 5).

In one preferred embodiment, the reading apparatus further comprises a buzzer 150 for promoting the detection process or the detection results (FIG. 5).

In one preferred embodiment, the reading apparatus comprises a base board 60 and a base frame 70, wherein the light emitting element and the photodetector are located on the base board 60, and the base board 60 is a strip-shaped circuit board structure, for example, a PCB board. The base frame 70 has a detection window 701. The first light blocking element 301, the second light blocking element 302, the third light blocking element 303, the fourth light blocking element 304 and the fifth light blocking element 305 are located in the detection window 701. In one particular embodiment, the light blocking element is connected to the inner wall of the detection window 701, wherein the first light blocking element 301 and the third light blocking element 303 form mutually parallel structures in the detection window 701, and the second light blocking element 302 with the first light blocking element 301 and the third light blocking element 303 respectively forms a mutually perpendicular structure, the fourth light blocking element 304 and the first light blocking element 301, the fifth light blocking element 305 and the third light blocking element 303 form mutually perpendicular structures. In one preferred embodiment, the fourth light blocking element 304, the fifth light blocking element 305 may be separate components connected to the detection window 701, or may be constituted by a part extended by the detection window 701. Further, the above light blocking element and the base frame 70 may be integrally formed (FIG. 2 and FIG. 5).

In one preferred embodiment, the processor is a circuit system, and the processor, the display 130, the power supply element 140 and the buzzer 150 are disposed on the base board 60.

The base board 60 is located on one side of the detection window 701, the testing element 40 is located on the other side of the detection window 701, and the base board 60 and the base frame 70 may be detachable combination. When the base board 60 is combined with the base frame 70 and the testing element 40 is fixed on the base frame 70, and the detection window 701 encloses the first light-emitting element 101, the second light-emitting element 102, the first photodetector 201, and one or more areas of the testing element 40 in a closed space. At this time, the first light blocking element 301 and the third light blocking element 303 are seamlessly abutted with the mounting planes of the light emitting element 101/102 and the first photodetector 201, to separate the first light-emitting element 101 and the second light-emitting element 102 from the first photodetector 201, respectively; the second light blocking element 302 is seamlessly abutted with the testing element 40, to separate one or more areas of the testing element 40, preferably, to separate the testing area 403 and the control area 405 of the testing element, and block the light from an area of the testing element 40 that is covered by the second light blocking element 302 from entering the first photodetector 201; The fourth light blocking element 304 is in seamlessly abutted with the testing element 40, to block the light from the first light-emitting element 101 from illuminating the area in front of the testing area of the testing element; the fifth light blocking element 305 is seamlessly abutted with the testing element 40, to block the light from the second light-emitting element 102 from illuminating the area behind the control area of the testing element. In one particular embodiment, the light emitted from the first light-emitting element 101 and the second light-emitting element 102 illuminates the testing area 403 and the control area 405 of the testing element through the third gap 503 and the fourth gap 504, respectively; and the light from the testing area 403 and the control area 405 of the testing element is received by the first photodetector 201 through the first gap 501 and the second gap 502, and is converted into an electrical signal that can be detected by the processor. The light blocking element herein can perform additional functions, for example, properly supporting the testing element 40, and keeping the testing element 40 and the light emitting element and/or the photodetector at an appropriate distance (FIG. 3).

In the present embodiment, the testing element 40 may be a separate component that is introduced into the reading apparatus, and the testing element 40 is fixed in the slot 702 on the base frame 70 (FIG. 4). In one particular embodiment, the testing element 40 is provided with a sample application stick 110 close to one end of the detection area 403. The sample application stick 110 is a commonly used lateral-flow sample application stick, and one end thereof is connected to the sample absorption area 401 of the testing element 40, that is, the sample absorption area 401 of the testing element 40 is overlapped on the sample application stick 110, and the other end thereof is used to contact the sample (FIG. 5). The sample application stick 110 is fixed on the tray 703 disposed at one end of the base frame 70. The tray 703 is not on the same horizontal plane as the slot 702 connected to the testing element 40, and the position of the tray 703 is lower than the slot 702. When the sample application stick 110 is fixed on the tray 703, the sample application stick 110 is substantially flush with the testing element 40 or the slot 702 where the testing element is placed. The tray 703 has a protrusion 704 on the surface that is in contact with the sample application stick 110, and the protrusion 704 can be inserted into the sample application stick 110 to fix the sample application stick 110 (FIG. 4). During use, samples are absorbed by the sample application stick 110 and transferred by the testing element 40.

In one particular embodiment, the reading apparatus has a conduction device for activating or waking up the reading apparatus. In one particular embodiment, the conduction device is a front conduction electrode 120, and one end of the front conduction electrode 120 is connected to the sample application stick 110, and the other end is connected to the front electrode contact of the reading device conduction circuit. In one particular embodiment, the front conductive electrode 120 is disposed in the tray 703 for fixing the sample application stick 110 and is connected to the sample application stick 110. Specifically, the front conduction electrode 120 is located between the tray 703 and the sample application stick 110. After the sample application stick 110 sucks samples, when liquid flows through the front conduction electrode 120, the detection system is switched on, and the device starts self-test. The front conduction electrode 120 is disposed between the tray 703 and the sample application stick 110, to ensure that the front conduction electrode 120 is in good contact with the sample application stick 110. During use, the sample application stick 110 may be displaced due to collision or improper operation, which causes the front conduction electrode 120 unable to be in contact with the sample application stick 110 effectively. The apparatus of the present invention can effectively prevent non-conduction or non-activation caused by poor contact between the front conduction electrode 120 and the sample application stick 110 (FIG. 5).

In preferred embodiments, the reading apparatus may further comprise a housing. The function of housing is to support the components of the reading apparatus and/or protect them from the influence of the external environment. The housing can be formed into an optimum shape with a carbonized plastic such as polystyrene or ABS (acrylonitrile-butadiene-styrene). The housing consists of an upper casing 80, a lower casing 90, and a cover body 100. The upper casing 80, the lower casing 90 and the cover body 100 cooperate to form a hollow housing. In the present embodiment, the upper casing 80, the lower casing 90 and the cover body 100 are detachably combined together by a snap, to facilitate assembly. The upper casing 80 has a window for observing the test results. The structure of the housing is not limited thereto, and the detachable combination of the upper casing 80, the lower casing 90, and the cover body 100 is not limited to a snap, for example, a method such as a screw is also suitable for the present invention. The sample application stick 110 is exposed through the opening at one end of the housing, to facilitate samples drawing (FIG. 5).

The reading apparatus is in a low power dominant state when not in use. When samples are drawn by the sample application stick 110, the liquid sample flows through the front conduction electrode 120 to achieve conduction and activate the reading apparatus. This apparatus will be awaken and activated in approximately 5-15 seconds, to start self-test immediately and check the calibration parameters.

In one particular embodiment, when the sample is added to the testing element 40 for a period of time (this period of time refers to the time that the analyte in the sample has reaction with the detection substance preset on the testing element, usually it is 5 to 10 minutes). The processor controls two light emitting elements to alternately emit light according to the time sequence, to illuminate the testing area 403 and the control area 405 of the testing element respectively. The light is reflected in the area where light is received, and the reflected light illuminates the photodetector 201 through the first gap 501 and the second gap 502. The photodetector 201 detects out the corresponding electrical signal or voltage respectively, feeds back the detection information to the processor, and the processor performs analysis and determination according to the received detection information.

Example 2

In the present embodiment, the present invention provides a reading apparatus for reading an assay result on a testing element, wherein the apparatus comprising: a first light-emitting element 101 and a second light-emitting element 102, disposed in positions corresponding to the testing area 403 and the control area 405 of the testing element respectively, emitting light and illuminating corresponding areas of the testing element 40; a first photodetector 201 and a second photodetector 202, disposed opposite the first light-emitting element 101 and the second light-emitting element 102, respectively, for receiving light from corresponding areas of the testing element 40; and a light blocking element, for guiding a path of light emitted from a light emitting element and/or from a testing element, to separate the two photodetectors in separate spaces (FIG. 7).

In the present embodiment, the first light-emitting element 101 and the second light-emitting element 102 are light emitting diodes, specifically LED lights, and the first photodetector 201 and the second photodetector 202 are photodiodes (PD) for detecting light illuminating thereon and converting it into a detectable electrical signal.

In the present embodiment, the first light-emitting element 101 and the second light-emitting element 102 are linearly arranged, and the first photodetector 201 and the second photodetector 202 are linearly arranged. The first light-emitting element 101 and the first photodetector 201, the second light-emitting element 102 and the second photodetector 202 are linearly arranged respectively.

In the present embodiment, there is a gap 50 on the light blocking element that separates the first photodetector 201 to allow the light from the testing area 403 of the testing element to transmit. The gap 50 is disposed at a position corresponding to the testing area 403 of the testing element, includes a first gap 5011 and the second gap 5012, and the first gap 5011 is connected to the second gap 5012; and there is a gap 50 on the light blocking element that separates the second photodetector 202 to allow light from the control area 405 of the testing element to transmit, and the gap 50 is disposed at a position corresponding to the control area 405 of the testing element, includes a first gap 5011 and the second gap 5012, and the first gap 5011 is connected to the second gap 5012.

Wherein, the light blocking element comprising the first light blocking element 3011, the third light blocking element 3031, the fourth light blocking element 3041 and the fifth light blocking element 3051 encloses the first photodetector 201 in a separate space, and the first light blocking element 3011 has a first gap 5011, the side of the first gap 5011 adjacent to the first light-emitting element 101 and the first photodetector 201 is a slope, and there is a second gap 5012 between the fourth light blocking element 3041 and the fifth light blocking element 3051, and the width of the first gap 5011 is equal to that of the second gap 5012, thereby forming a L-shaped gap 50 on the light blocking element that encloses the first photodetector 201, such that the light emitted from the first light-emitting element 101 illuminates the testing area 403 as much as possible, and the light from the testing area 403 can enter the first photodetector 201, to effectively avoid the invalid light in the area near the testing area from entering the first photodetector 201. Wherein, the light blocking element comprising the sixth light blocking element 3061, the eighth light blocking element 3081, the ninth light blocking element 3091 and the tenth light blocking element 3101 encloses the second photodetector 202 in a separate space, and the sixth light blocking element 3061 has a first gap 5011, the side of the first gap 5011 adjacent to the second light-emitting element 102 and the second photodetector 202 is a slope, and there is a second gap 5012 between the ninth light blocking element 3091 and the tenth light blocking element 3101, and the width of the first gap 5011 is equal to that of the second gap 5012, thereby forming a L-shaped gap 50 on the light blocking element that encloses the second photodetector 202, such that the light emitted from the second light-emitting element 102 illuminates the control area 405 as much as possible, and the light from the control area 405 can enter the second photodetector 202, to effectively avoid the invalid light in the area near the control area from entering the second photodetector 202. By the foregoing optical path optimization, the optical path and the light illumination area are further effectively defined to enhance the sensitivity and accuracy of the detection result.

In the present embodiment, when the testing element 40 is fixed on the electronic reading apparatus, the fourth light blocking element 3041, the fifth light blocking element 3051, the ninth light blocking element 3091, and the tenth light blocking element 3101 are in contact with the testing element 40 and are longitudinally parallel with the testing element 40, and the longitudinal extension of the first light blocking element 3011, the third light blocking element 3031, the sixth light blocking element 3061, and the eighth light blocking element 3081 intersects the testing element 40.

In the present embodiment, the electronic reading apparatus further comprises a third photodetector 203 located between the first light-emitting element 101 and the second light-emitting element 102. The third photodetector 203 is linearly arranged with the first light-emitting element 101 and the second light-emitting element 102 for initial calibration or dimming of the electronic reading apparatus.

In the present embodiment, the apparatus comprises a lateral flow testing element 40. As described above, the testing element 40 can be a separate device that is introduced into the reading apparatus for analyte detection, or the testing element 40 is an integral part of the reading apparatus. If the testing element is an integral part of the reading apparatus, the reading apparatus may comprise a testing element 40 for microfluidic detection or lateral chromatographic detection.

In the present embodiment, the reading apparatus may comprise a slot or other opening for accommodating the testing element 40 to insert to the reading apparatus. The shape and size of the slot or opening should allow successful insertion of a testing element 40 in an appropriate direction.

In the present embodiment, the reading apparatus comprises a processor for receiving electrical signals and performing analysis and result determination. The processor controls the two light emitting elements to sequentially emit light and illuminate the testing area 403 and control area 405 of the testing element 40. The first photodetector and the second photodetector sequentially receive the light from the testing area 403 and the control area 405 and convert it into an electrical signal, and the processor receives the electrical signal of the photodetector for reading and analysis.

In the present embodiment, the reading apparatus further comprises a display 130 and a power supply element 140. The processor displays the processing result on the display 130 to facilitate observation of the detection results. The power supply element 140 provides power for the entire photodetection system, for example, a power supply element such as a button battery may be used (FIG. 13).

In the present embodiment, the reading apparatus further comprises a buzzer 150 for promoting the detection process or the detection results.

In the present embodiment, the reading apparatus comprises a base board 60 and a base frame 70, wherein the light emitting element and the photodetector are located on the base board 60, and the base board 60 is a strip-shaped circuit board structure, for example, a PCB board. The base frame 70 has a detection window 701. The light blocking element is located in the detection window 701. In one particular embodiment, the light blocking element 30 is located in the detection window 701, wherein the fifth light blocking element 3051 and the tenth light blocking element 3101 may be separate components connected to the detection window 701, or may be constituted by a part extended inwardly by the detection window 701. Further, the light blocking element 30 and the base frame 70 may be integrally formed (FIG. 8 and FIG. 13).

In the present embodiment, the processor is a circuit system, and the processor, the display 130, the power supply element 140 and the buzzer 150 are disposed on the base board 60.

In the present embodiment, the base board 60 is located on one side of the detection window 701, the testing element 40 is located on the other side of the detection window 701, and the base board 60 and the base frame 70 may be detachable combination. When the base board 60 is combined with the base frame 70 and the testing element 40 is fixed on the base frame 70, and the detection window 701 encloses the first light-emitting element 101, the second light-emitting element 102, the first photodetector 201, the second photodetector 202 and the third photodetector 203, and one or more areas of the testing element 40 in a closed space. At this time, the first light blocking element 3011, the third light blocking element 3031, the sixth light blocking element 3061 and the eighth light blocking element 3081 are seamlessly abutted with the mounting planes of the light emitting element 101/102 and photodetectors 201~203 to separate the first light-emitting element 101 and the second light-emitting element 102 from the first photodetector 201 and the second photodetector 202, and separate first photodetector 201 from the second photodetector 202. The fourth light blocking element 3041, the fifth light blocking element 3051, the ninth light blocking element 3091 and the tenth light blocking element 3101 is in seamlessly abutted with the testing element 40, to cover one or more areas of the testing element, preferably cover partial areas in front of and behind the testing area and in front of and behind the control area, which, on one hand, blocks the light emitted from the light emitting element from illuminating the covered area, and on the other hand, blocks the light from the covered area from entering the photodetector. The light from the testing area and the control area of the testing element is received by two photodetectors through a gap respectively, and convert it into an electrical signal that can be detected by the processor. The light blocking element herein can perform additional functions, for example, properly supporting the testing element 40, and keeping the testing element 40 and the light emitting element and/or the photodetector at an appropriate distance.

In the present embodiment, the testing element 40 may be a separate component that is introduced into the reading apparatus, and the testing element 40 is fixed in the slot 702 on the base frame 70. In the present embodiment, the testing element 40 is provided with a sample application stick 110 close to one end of the detection area 403. The sample application stick 110 is a commonly used lateral-flow sample application stick, and one end thereof is connected to the sample absorption area 401 of the testing element 40, that is, the sample absorption area 401 of the testing element 40 is overlapped on the sample application stick 110, and the other end thereof is used to contact the sample (FIG. 13). The sample application stick 110 is fixed in the groove 7031 disposed at one end of the base frame 70. The groove 7031 is not on the same horizontal plane as the slot 702 connected to the testing element 40, and the position of the groove 7031 is lower than the slot 702. When the sample application stick 110 is fixed in the groove 7031, the sample application stick 110 is substantially flush with the testing element 40 or the slot 702 where the testing element is placed. The groove 7031 has a protrusion 704 on the surface that is in contact with the sample application stick 110, and the protrusion 704 can be inserted into the sample application stick 110 to fix the sample application stick 110 (FIG. 7). During use, samples are absorbed by the sample application stick 110 and transferred by the testing element 40.

In the present embodiment, the electronic reading apparatus has a conduction device for activating or waking up the reading apparatus. The conduction device is a front conduction electrode 120, and the front conduction electrode 120 is disposed in the way as described in the Example 1. In the present embodiment, the electronic reading apparatus also comprises a housing as described in Example 1.

In the present embodiment, the processor controls two light emitting elements to alternately emit light according to the time sequence, to illuminate the testing area 403 and the control area 405 of the testing element respectively. The light is reflected in the area where light is received, and the reflected light illuminates the first photodetector 201 and the second photodetector 202 through the gap 50. The first photodetector 201 and the second photodetector 202 detect out the corresponding electrical signal or voltage respectively, feed back the detection information to the processor, and the processor performs analysis and determination according to the received detection information.

The invention shown and described herein may be implemented in the absence of any elements, limitations specifically disclosed herein. The terms and expressions used herein are for illustration rather than limitation, which do not exclude any equivalents of the features and portions described herein in the use of these terms and expressions, in addition, it should be understood that various modifications are feasible within the scope of the present invention. It is therefore to be understood that, although the invention has been particularly disclosed by various embodiments and alternative features, modifications and variations of the concepts described herein may be employed by those of skilled in the art, and such modifications and variations will fall into the scope of protection of the present invention as defined by the appended claims.

The contents of the articles, patents, patent applications, and all other documents and electronic information available or documented herein are incorporated herein by reference in their entirety, as if each individual publication is specifically and individually indicated for reference. The applicant reserves the right to incorporate any and all materials and information from any such article, patent, patent application or other document into this application.

The invention claimed is:

1. A reading apparatus for reading an assay result on a testing element, comprising:
   a first light-emitting element and a second light-emitting element for emitting light and illuminating one or more corresponding areas of the testing element;
   a first photodetector for receiving light from one or more corresponding areas of the testing element; and
   a light blocking element, for guiding a path of light emitted from a light emitting element and/or from the testing element, wherein the light blocking element comprises a first light blocking element and a second light blocking element, the first light blocking element is located between the first light-emitting element and the first photodetector to guide the light emitted from the light emitting element to illuminate the testing element, and the second light blocking element is located above the first photodetector; wherein the light blocking element further comprises a third light blocking element, and the first photodetector is located between the first light blocking element and the third light blocking element;
   a second photodetector, disposed outside the third light blocking element; and
   a third photodetector located between the first light-emitting element and the second light-emitting element for initial calibrations.

2. The reading apparatus according to claim 1, wherein the second light blocking element is disposed between the first photodetector and the testing element.

3. The reading apparatus according to claim 1, wherein the extension of the first light blocking element intersects the testing element, and the second light blocking element is longitudinally parallel to the testing element.

4. The reading apparatus according to claim 1, wherein the second light blocking element and the first light blocking element are disposed in a mutually perpendicular form.

5. The reading apparatus according to claim 1, wherein the second light blocking element is located between the first light blocking element and the third light blocking element and covers the first photodetector.

6. The reading apparatus according to claim 5, wherein the second light blocking element is disposed in an area between the testing area and the control area of the testing element.

7. The reading apparatus according to claim 1, wherein the first light-emitting element and the first photodetector are linearly arranged, or the first light-emitting element and/or the second light-emitting element are/is linearly arranged with the first photodetector.

8. The reading apparatus according to claim 1, wherein the second light blocking element is disposed in a testing area or a control area of the testing element.

9. The reading apparatus according to claim 1, wherein the light blocking element has a gap that transmits light from the testing element.

10. The reading apparatus according to claim 9, wherein the gap is disposed at a position corresponding to a testing area or a control area of the testing element.

11. The reading apparatus according to claim 9, wherein the gap is formed by providing a certain space between the first light blocking element and the second light blocking element.

12. The reading apparatus according to claim 11, wherein the gap is a slanted gap.

13. The reading apparatus according to claim 9, wherein the gap comprises a first gap and/or a second gap, the first light blocking element has a first gap, and/or the second light blocking element has a second gap.

14. The reading apparatus according to claim 13, wherein the second gap is in communication with the first gap.

15. The reading apparatus according to claim 1, further comprising a lateral flow testing element, wherein the testing element comprises a testing area and a control area.

* * * * *